United States Patent
Ouchi et al.

(10) Patent No.: US 6,852,077 B2
(45) Date of Patent: Feb. 8, 2005

(54) COVER FOR PREVENTING CONTAMINATION OF AN OPERATING PORTION OF AN ENDOSCOPE

(75) Inventors: Teruo Ouchi, Saitama (JP); Kazuyuki Yamamoto, Tokyo (JP)

(73) Assignee: PENTAX Corporation, Tokyo (JP)

(*) Notice: Subject to any disclaimer, the term of this patent is extended or adjusted under 35 U.S.C. 154(b) by 110 days.

(21) Appl. No.: 10/284,289

(22) Filed: Oct. 31, 2002

(65) Prior Publication Data

US 2003/0097043 A1 May 22, 2003

(30) Foreign Application Priority Data

| Nov. 1, 2001 | (JP) | P2001-336100 |
| Nov. 7, 2001 | (JP) | P2001-341707 |
| Nov. 7, 2001 | (JP) | P2001-342104 |
| Nov. 7, 2001 | (JP) | P2001-342105 |
| Mar. 6, 2002 | (JP) | P2002-060139 |
| Mar. 6, 2002 | (JP) | P2002-060140 |

(51) Int. Cl.⁷ ............................................. A61B 1/00
(52) U.S. Cl. .................... 600/122; 600/124; 600/125
(58) Field of Search ................................ 600/121, 122, 600/123, 124, 125

(56) References Cited

U.S. PATENT DOCUMENTS

| 4,825,850 A | 5/1989 | Opie et al. |
| 4,878,485 A | * 11/1989 | Adair .......................... 600/122 |
| 5,359,991 A | * 11/1994 | Takahashi et al. ........... 600/122 |
| 5,363,843 A | * 11/1994 | Daneshvar ................... 128/897 |
| 5,630,787 A | 5/1997 | Yabe et al. |
| 5,674,180 A | * 10/1997 | Yabe et al. .................. 600/122 |
| 5,695,449 A | * 12/1997 | Moriyama .................... 600/122 |
| 5,924,977 A | * 7/1999 | Yabe et al. .................. 600/121 |

FOREIGN PATENT DOCUMENTS

| JP | 4-325138 | 11/1992 |
| JP | 6-237883 | 8/1994 |
| JP | 6-68708 | 9/1994 |
| JP | 8-33606 | 2/1996 |
| JP | 2746651 | 2/1998 |
| JP | 2984098 | 9/1998 |

* cited by examiner

Primary Examiner—Beverly M. Flanagan
(74) Attorney, Agent, or Firm—Greenblum & Bernstein, P.L.C.

(57) ABSTRACT

A cover for preventing contamination of an operating portion covered on an operating portion of an endoscope a lower end of which is connected with an inserting portion. The cover is formed in a bag-like shape for enveloping a total of the operating portion, formed with a hole for passing the inserting portion at a lower end portion thereof and formed with a sleeve-like portion for inserting the hand to directly hold the operating portion at a rear face thereof.

22 Claims, 33 Drawing Sheets

FIG. 3
FIG. 4
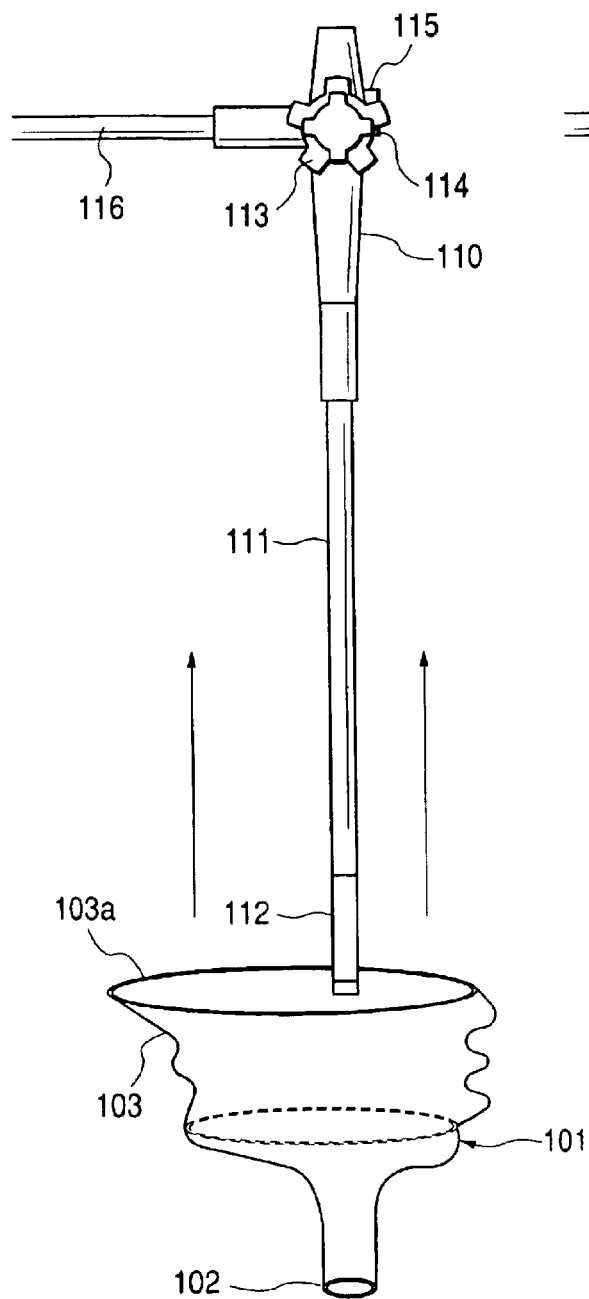
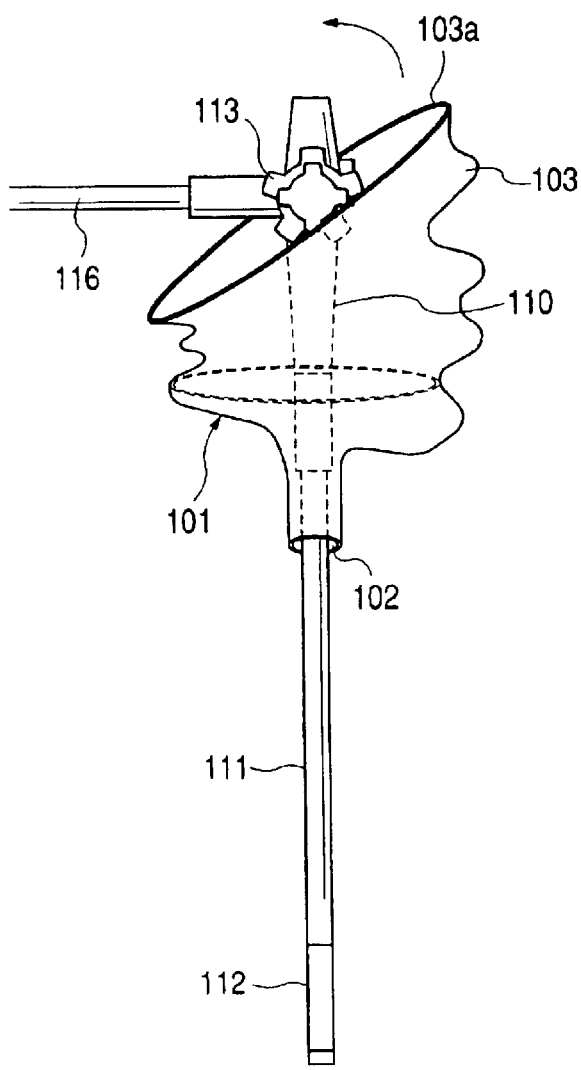

FIG. 14
FIG. 15
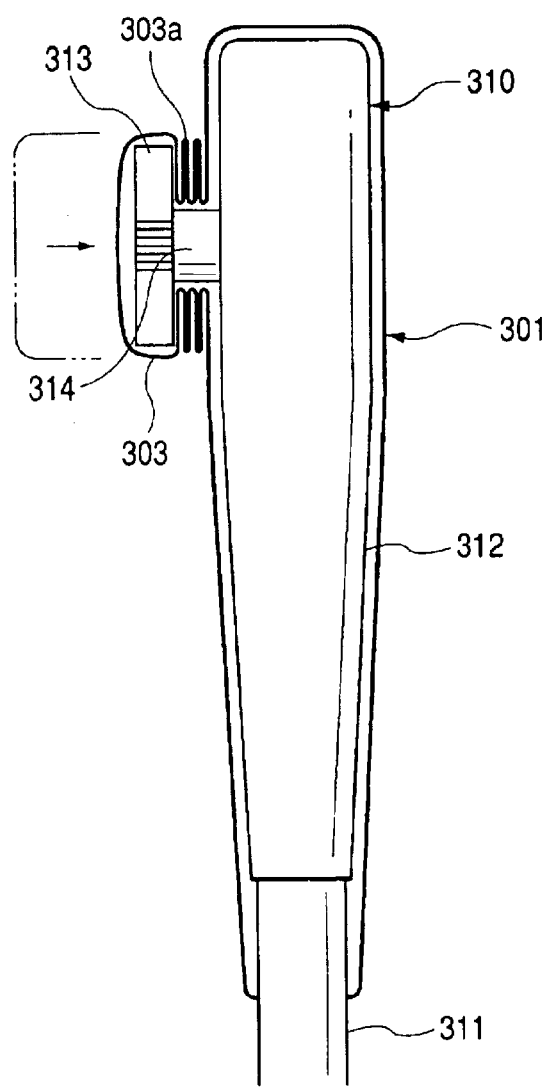
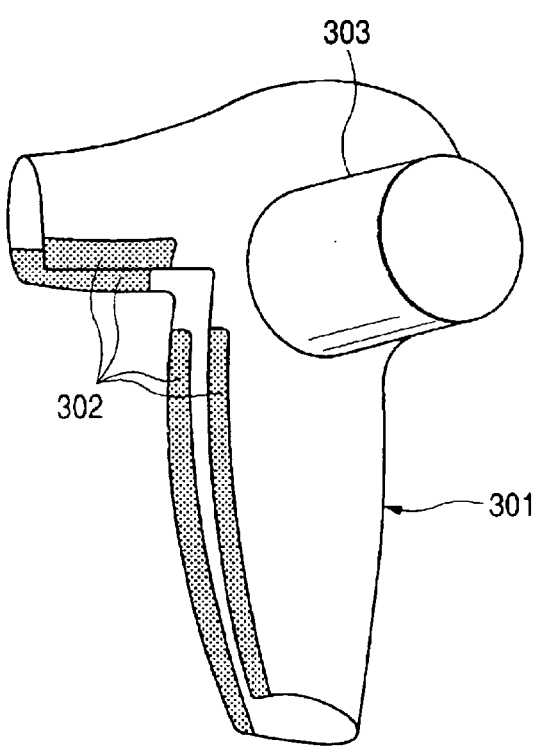

FIG. 20
FIG. 21
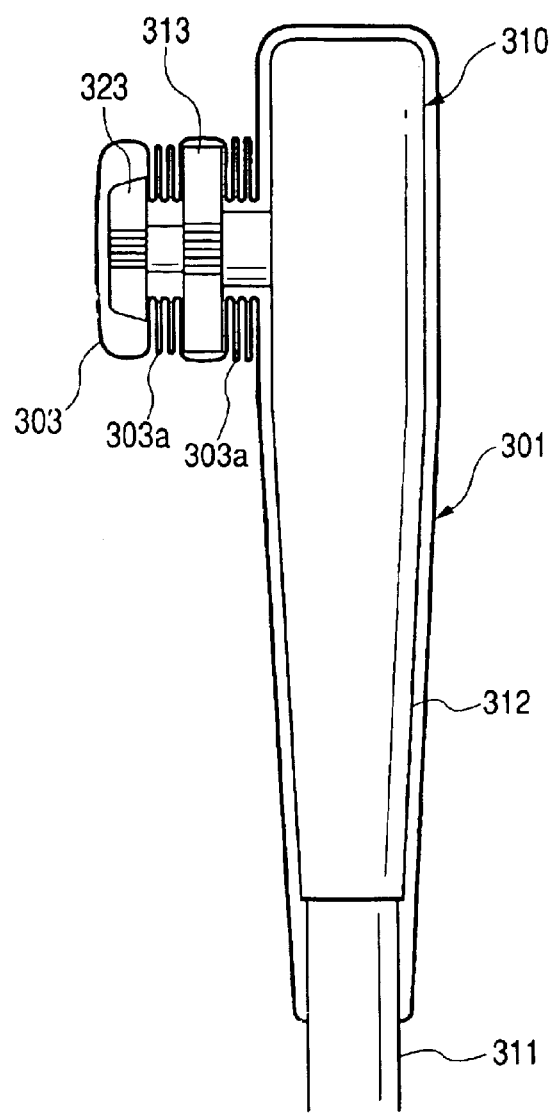
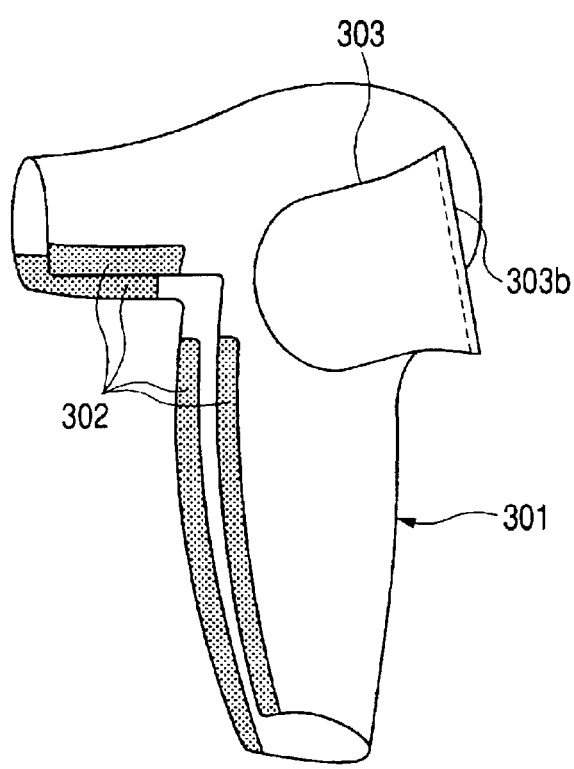

COVER FOR PREVENTING CONTAMINATION OF AN OPERATING PORTION OF AN ENDOSCOPE

BACKGROUND OF THE INVENTION

The present invention relates to a cover for preventing contamination of an operating portion of an endoscope for covering the operating portion of the endoscope such that the operating portion is not contaminated in using the operating portion.

In order to prevent infection from patient to patient via an endoscope from being brought about, it is preferable to cover an operating portion of the endoscope such that the operating portion is not contaminated.

Hence, there is a constitution in which an operating portion is used in a state of being enveloped by a cover in a sheet-like shape as shown by, for example, Japanese Patent Laid-Open No. 325138/1992, a constitution of enveloping a total of an operating portion by forming a cover enveloping the operating portion in a bag-like shape as shown by Japanese Utility Model Laid-Open No. 68708/1994 and the like.

1) In an operating portion of an endoscope, generally, a bending operating member for bending a bending portion formed at an inserting portion by remote operation, is projected sideways from an operating portion body and even in the case of an operating portion enveloped by a cover for preventing contamination, it is necessary to operate to rotate the bending operating member around an axis.

However, when the bending operating member is enveloped by the cover, the bending operating member is operated to rotate from an outer side of the cover and therefore, there is a drawback of significantly restricting operation of the bending operating member to thereby deteriorate bending operation performance (Japanese Utility Model Laid-Open No. 68708/1994).

Further, when a bending operating shaft is projected to outside of a cover from a hole formed at the cover and a bending operating knob is made to be attachable and detachable to and from the shaft in order to prevent the bending operation performance from being deteriorated, attachment and detachment and cleaning and disinfection of the bending operating knob become troublesome and further, there is a concern of making a dirty solution invade inside of the cover from the hole portion to thereby contaminate the operating portion (Japanese Patent Laid-Open No. 325138/1992).

Hence, it is an object of the invention to provide a cover for preventing contamination of an operating portion of an endoscope capable of firmly preventing contamination of an operating portion by enveloping the operating portion of an endoscope along with a bending operating member and capable of achieving excellent bending operation performance when the endoscope is used.

2) In the case of the related-art cover for preventing contamination of the operating portion of the endoscope, in any cases, an operator holds the operating portion by gripping the operating portion from an outer face of the cover and therefore, the hand does not become accustomed to the operating portion, and there is a case in which the operating portion is moved unintentionally in the hand during inspection by the endoscope or the operating portion is slipped off from the hand.

Further, since the hand of the operator for holding the operating portion from the outer face of the cover is contaminated by the inspection by the endoscope and therefore, there is a case in which the operator cannot touch peripheral apparatus by the hand or the operator cannot hang the endoscope on an hanger after finishing the inspection, which is considerably inconvenient.

Hence, it is another object of the invention to provide a cover for preventing contamination of an operating portion of an endoscope by which an operator can stably hold an operating portion of an endoscope and the hand of the operator holding the operating portion is not contaminated.

3) According to the related-art cover apparatus for preventing contamination of the operating portion of the endoscope, an air feed and water feed operating valve and a suction operating valve communicated and connected to an air feed and water feed path and a suction path are entirely enveloped by the cover along with a total of the operating portion.

The air feed and water feed operating valve or the suction operating valve or the like is generally constructed by a constitution in which a path switching member in a piston-like shape is extractably and retractably arranged at inside of a cap in a shape of a cylinder connected with a base end of the air feed and water feed path or the suction path.

Therefore, for example, a dirty solution invades, for example, inside of the cap of the suction operating valve via the inside of the suction path and there is a concern that when a seal of the switch valve is malfunctioned even slightly, the dirty solution leaks out from the gap into the cover, and the operating portion is contaminated.

Hence, it is yet another object of the invention to provide a cover apparatus for preventing contamination of an operating portion of an endoscope which is hygienically highly safe with no concern of contaminating the operating portion even when a dirty solution is leaked from a cap arranged to the operating portion by being communicated and connected to a path opened to a front end of an inserting portion.

4) Generally, in an endoscope inspecting room, a clean endoscope before use is brought into a state of holding an operating portion thereof at a holding member such as an endoscope hanger or the like to be able to use immediately after preparing a patient.

However, when the related-art cover for preventing contamination of an operating portion is covered on the operating portion, it is necessary to remove the operating portion from the operating portion holding member and therefore, there is a concern of contaminating or destructing an inserting portion at that occasion.

Hence, it is still another object of the invention to provide a cover for preventing contamination of an operating portion of an endoscope capable of easily covering the operating portion of the endoscope in a state of being held by an operating portion holding member.

SUMMARY OF THE INVENTION

To achieve at least one of the above-noted objects, the present invention provides the followings preferable arrangements:

A cover for preventing contamination of an operating portion of an endoscope according to the invention is a cover for preventing contamination of an operating portion covered on the operating portion of the endoscope, a lower end of the operating portion being connected with an inserting portion. The cover is formed in a bag-like shape for enveloping a total of the operating portion. The cover is formed with a hole for passing the inserting portion of the endoscope at a lower end portion thereof. The cover is formed with a sleeve-like portion for inserting a hand of an operator to directly hold the operating portion at a rear face thereof.

Further, a light guide cable extended from the operating portion and connected to a light source apparatus may be passed through the sleeve-like portion. A second sleeve-like portion for passing the light guide cable extended from the operating portion and connected to the light source apparatus may be provided separately from the sleeve-like portion for inserting the hand.

Another cover for preventing contamination of an operating portion of an endoscope according to the invention is a cover for preventing contamination of an operating portion of an endoscope for covering the operating portion of the endoscope having a constitution in which a bending operating member operated to rotate around an axis for bending a bending portion provided at an inserting portion by a remote operation, is provided to project from an operating portion body connected to a base end of the operating portion. The cover is formed by a flexible material to envelope a total of the operating portion, and a flexible ring-like band for tightening the cover from an outer side in a direction of an axial position of a rear side of the bending operating member.

Further, a sleeve-like portion for inserting the hand for holding the operating portion into the cover may be formed at the cover. The bending operating member may include a plurality of operating knobs arranged to shift positions thereof in an axial direction such that the plurality of operating knobs are operated to rotate independently from each other and the ring-like bands may be provided in correspondence with a number of the bending operating knobs to tighten the plurality of operating knobs respectively by the cover.

Yet another cover for preventing contamination of an operating portion of an endoscope according to the invention is a cover for covering an operating portion of an endoscope having a constitution in which a bending operating member operated to rotate around an axis for bending a bending portion provided at an inserting portion by remote operation, is attached to a shaft member projected from an operating portion body connected to a base end of the inserting portion. The cover is formed to envelope the operating portion by a flexible material, and in which a portion thereof enveloping the bending operating member is arranged in a state of being folded in a bellows-like shape at a space between the bending operating member and a surface of the operating portion body by being formed in a shape of a cylinder a projected end portion of which is closed and pushed to crush in an axial line direction.

Further, the bending operating member may include two operating knobs arranged by shifting positions thereof in the axial line direction to be operated to rotate independently from each other, and the cylindrical portion may be arranged in the state of being folded in the bellows-like shape by being pushed to crush in the axial line direction even at a portion between the two operating knobs.

Still another cover for preventing contamination of an operating portion of an endoscope according to the invention is a cover for preventing contamination of an operating portion of an endoscope for covering the operating portion of the endoscope having a constitution in which a cap communicated and connected to a path opened to a front end of an inserting portion is arranged at the operating portion. The cover is formed by a flexible material for enveloping the operating portion and bored with a hole for projecting an end portion opening of the cap to an outer side, and a cap fixing member for fixing the cover and the cap is provided in a state in which the end portion opening of the cap is projected to an outer side of the cover.

Further, the path may be an air feed and water feed path or a suction path, the cap may be a cylinder of an air feed and water feed operating valve or a cylinder of a suction operating valve and the path may be a treating piece inserting channel for inserting a treating piece and the cap may be a treating piece inserting cap for inserting the treating piece.

Further another cover for preventing contamination of an operating portion of an endoscope of the invention is a cover for preventing contamination of an operating portion of an endoscope for covering the operating portion connected with a base end of an inserting portion at a lower end thereof. In the cover, a rear portion and a lower portion are continuously formed to open serially, and other portion is formed in a bag-like shape loosely surrounding the operating portion. An edge portion shape maintaining member is provided for maintaining a shape of the portion to a degree of not deforming the shape along an opening edge portion of the rear portion. A lower half portion of the rear portion is arranged with an openable and closable closed state maintaining member capable of maintaining the portion in a closed state.

Further, by forming an opening of an upper half portion of the rear portion such that the operating portion can directly be gripped by the hand of the operator by inserting the hand of the operator to inside thereof from the opening, the endoscope can be used without contaminating the hand.

Further, the edge portion shape maintaining member may be a wire or a strip-like member made of a metal or made of plastic attached continuously or discontinuously along the opening edge portion of the rear portion and the closed state maintaining member may be a member in a hook-like shape provided at a vicinity of the opening edge portion of the rear portion.

Further, a trough-like member for restricting a dirty solution from flowing to an inner side of the opening edge portion along an outer surface side of the opening edge portion of the rear portion and in that case, the trough-like member may also serve as the edge portion shape maintaining member.

A still further cover for preventing contamination of an operating portion of an endoscope according to the invention is a cover for preventing contamination of an operating portion of an endoscope for covering the operating portion of the endoscope, a lower end of the operating portion being connected with a base end of an inserting portion, and a side portion of the operating portion being connected with a base end of a light guide cable. By the cover, both of a vicinity of the base end of the light guide cable and an operating portion holding member are covered along with the operating portion in a state in which the operating portion is held by the operating portion holding member for holding the operating portion.

Further, the cover for preventing contamination of the operating portion may be formed in a bag-like shape including a sleeve-like portion for successively passing the inserting portion and the operating portion and setting the inserting portion and the operating portion at a position of surrounding both of a vicinity of the base end of the light guide cable and the operating portion holding member and a small opening for passing the inserting portion and setting the inserting portion to a vicinity of a portion of connecting the operating portion and the inserting portion.

Further, in that case, the sleeve-like portion may be formed such that an operator can hold directly the operating portion by inserting the hand from an outer side thereof.

The present disclosure relates to the subject matter contained in Japanese patent application Nos.:

P2001-336100 (filed on Nov. 1, 2001);
P2001-341707 (filed on Nov. 7, 2001);
P2001-342104 (filed on Nov. 7, 2001);
P2001-342105 (filed on Nov. 7, 2001);
P2002-060139 (filed on Mar. 6, 2002); and
P2002-060140 (filed on-Mar. 6, 2002),
which are expressly incorporated herein by reference in their entireties.

BRIEF DESCRIPTION OF THE DRAWINGS

FIG. 3 is an outline view showing motion of covering the cover on the operating portion according to the first embodiment of the invention.

FIG. 4 is an outline view showing the operation of covering the cover on the operating potion according to the first embodiment of the invention.

FIG. 14 is an outline front sectional view of a state of finishing to cover a cover on an operating portion according to a third embodiment of the invention.

FIG. 15 is a perspective view of the cover for preventing contamination of the operating portion of an endoscope according to the third embodiment of the invention.

FIG. 20 is a front sectional view of a state of finishing to cover the cover on the operating portion according to the modification of the third embodiment of the invention.

FIG. 21 is a perspective view of a cover for preventing contamination of an endoscope according to a modification of the third embodiment of invention.

DESCRIPTION OF THE PREFERRED EMBODIMENT

The present invention will be discussed with reference to preferred embodiments illustrated in the accompanying drawings.

First Embodiment

A main feature of a cover for preventing contamination of an operating portion of an endoscope according to this embodiment is such that the cover is formed in a bag-like shape enveloping the total of the operating portion, a lower end portion thereof is formed with a hole for passing an inserting portion of the endoscope, a rear face thereof is formed a the sleeve-like portion for inserting a hand of an operator to directly hold the operating portion. By this feature, the operator can stably hold the operating portion. Further, the hand of the operator is not contaminated by the inspection using the endoscope and therefore, the operator can touch peripheral apparatus by the hand and hangs the endoscope on a hanger after finishing the inspection.

Other features and advantages of the cover according to this embodiment are readily understandable from the description directed to this embodiment and/or the description directed to other embodiments.

Figure 2:
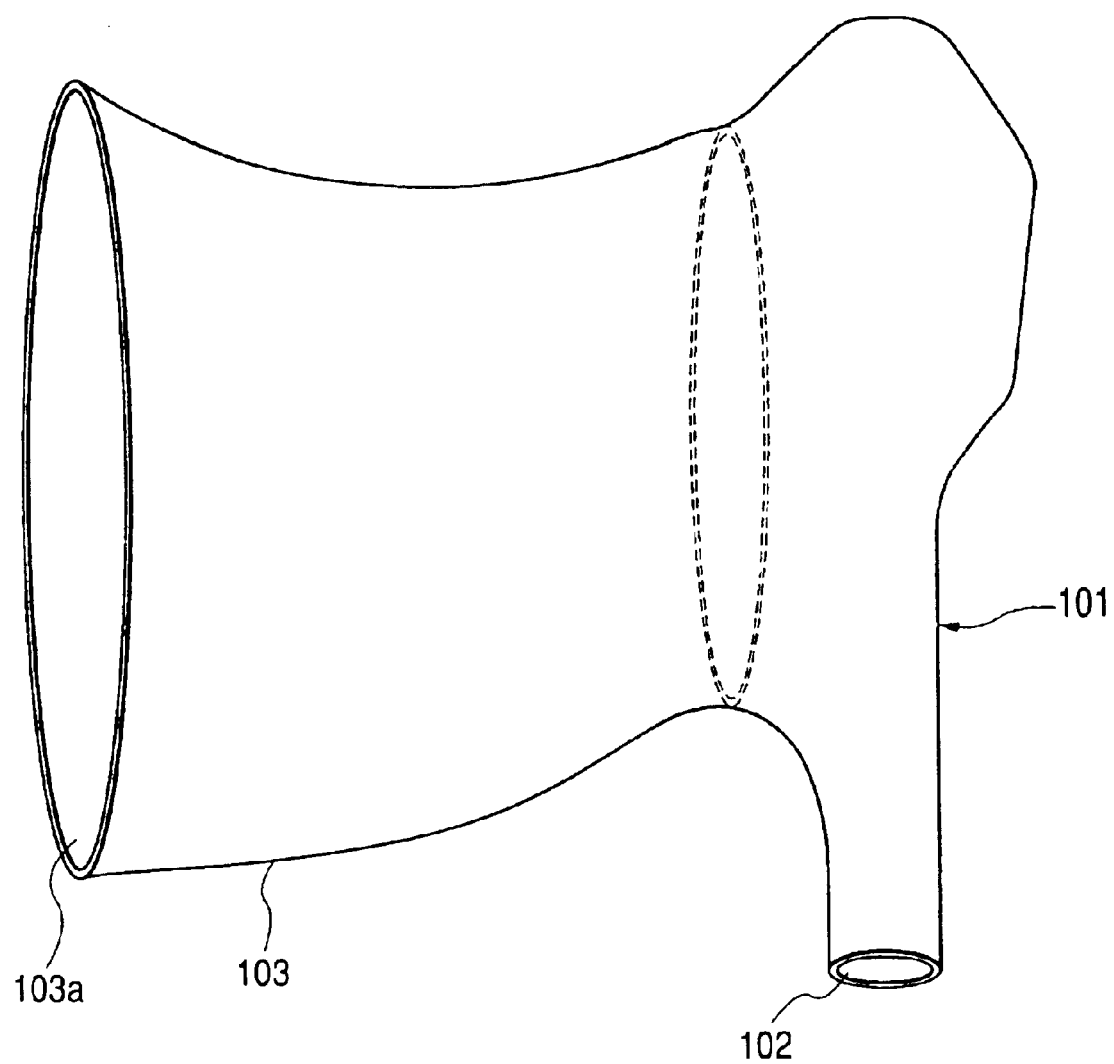
FIG. 2 is a side perspective view of the cover for preventing contamination of the operating portion of an endoscope according to the first embodiment of the invention.

FIG. 2 shows a single member of a cover 101 for preventing contamination of an operating portion of an endoscope. The cover 101 is formed in a bag-like shape enveloping a total of an operating portion of an endoscope, a lower end portion thereof is formed with a hole 102 for passing an inserting portion of the endoscope and a rear face thereof is formed with a sleeve-like portion 103 for inserting the hand to directly hold the operating portion. Notation 103a designates an end portion opening of the sleeve-like portion 103.

As a material of the cover 101, a sheet of a flexible synthetic resin material of, for example, polyethylene, polypropylene or the like or a sheet of an elastic rubber material can be used.

FIG. 3 shows a state before covering the cover 101 on an operating portion 110 of the endoscope and a front end of a flexible tube of an inserting portion 111 connected to a lower end of the operating portion 110 of the endoscope, is connected with a bending portion 112 bent by remote operation from the operating portion 110.

The operating portion 110 is arranged with a bending operating knob 113 for operating to bend the bending portion 112 as well as an air feed and water feed operating valve 114, a suction operating valve 115 and the like. Numeral 116 designates a light guide cable extended rearwardly from the operating portion 110 and connected to a light source apparatus, not illustrated.

When the cover 101 is covered on such an operating portion 110 of the endoscope, first, as shown by FIG. 3, the inserting portion of the endoscope (the flexible tube of the inserting portion 111, the bending portion 112) is passed from the end portion opening 103a to the sleeve-like portion 103 of the cover 101 and as shown by FIG. 4, the operating portion 110 is brought into a state of being contained in the cover 101 and the sleeve-like portion 103 is covered on the light guide cable 116.

Figure 1:
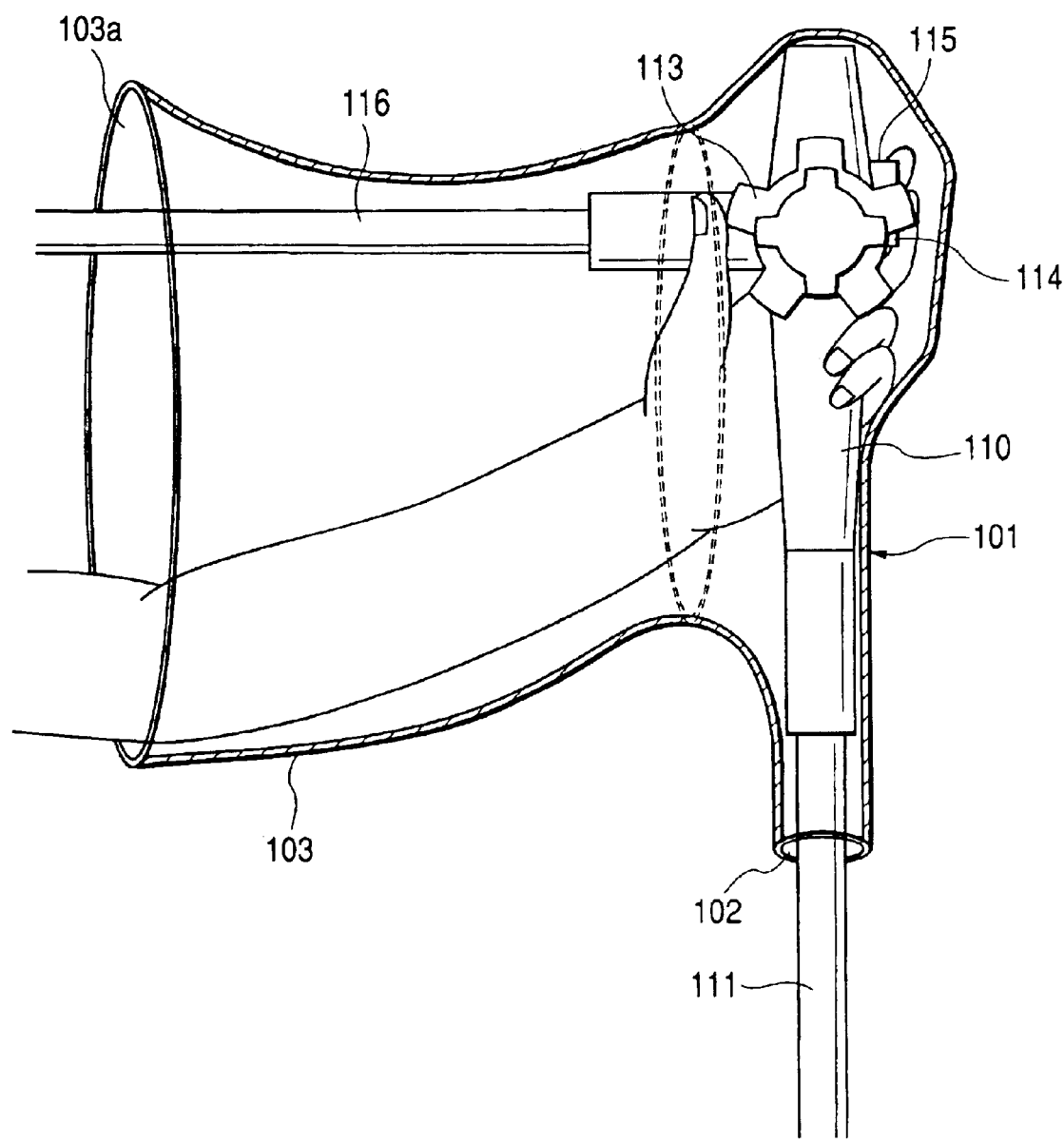
FIG. 1 is a side perspective view of a state of use in which a cover is covered on an operating portion according to a first embodiment of the invention.

In this way, as shown by FIG. 1, the cover 101 is brought into a state of entirely enveloping the operating portion 110 of the endoscope 110, the flexible tube 111 of the inserting portion 111 is extended downwardly by passing the hole 102 and the light guide cable 116 is brought into a state of being extended rearwardly from inside of the sleeve-like portion 103.

Then, the operator passes the hand from the end portion opening 103a into the sleeve-like portion 103 and holds the operating portion 110 in a stable state by directly gripping the operating portion 110 and the bending operating knob 113, the air feed and water feed operating valve 114 and the suction operating valve 115 and the like can be operated by the finger tips of the hands.

In this way, the hand of the operator holding the operating portion 110 is brought into a state of being surrounded by the cover 111 and is not contaminated by inspection by the endoscope and therefore, even when the operator touches peripheral apparatus by the hand and hangs the endoscope on an hanger after finishing the inspection, the surroundings are not contaminated.

Figure 5:
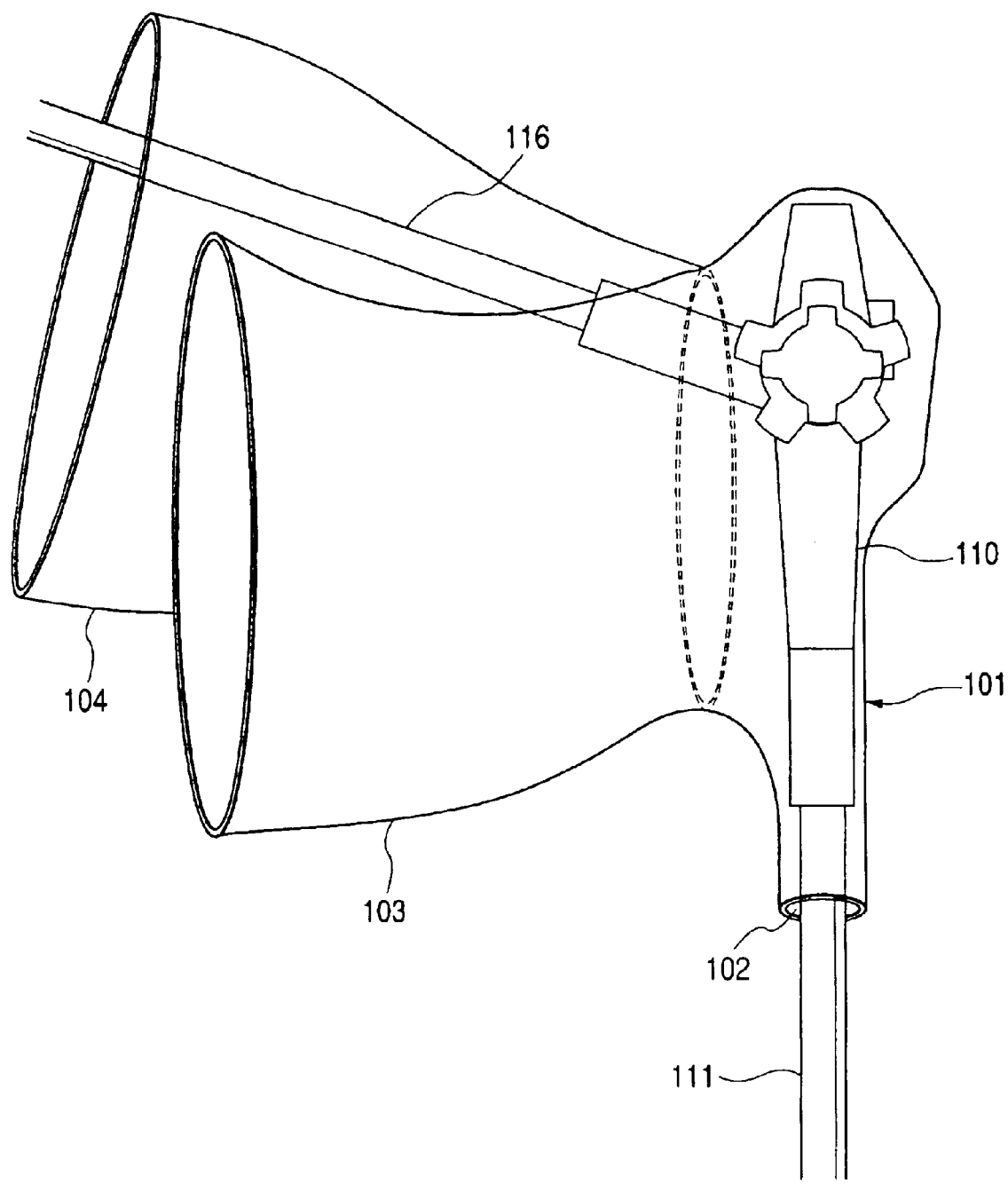
FIG. 5 is a side perspective view of a state of covering a cover on an operating portion according to a modification of the first embodiment of the invention.

Further, the invention is not limited to the above-described embodiment but as shown by, for example, FIG. 5, a second three-like portion 104 for passing the light guide cable 116 extended from the operating portion 110 and connected to the light source apparatus, maybe provided separately from the sleeve-like portion 103 for inserting the hand.

Figure 6:
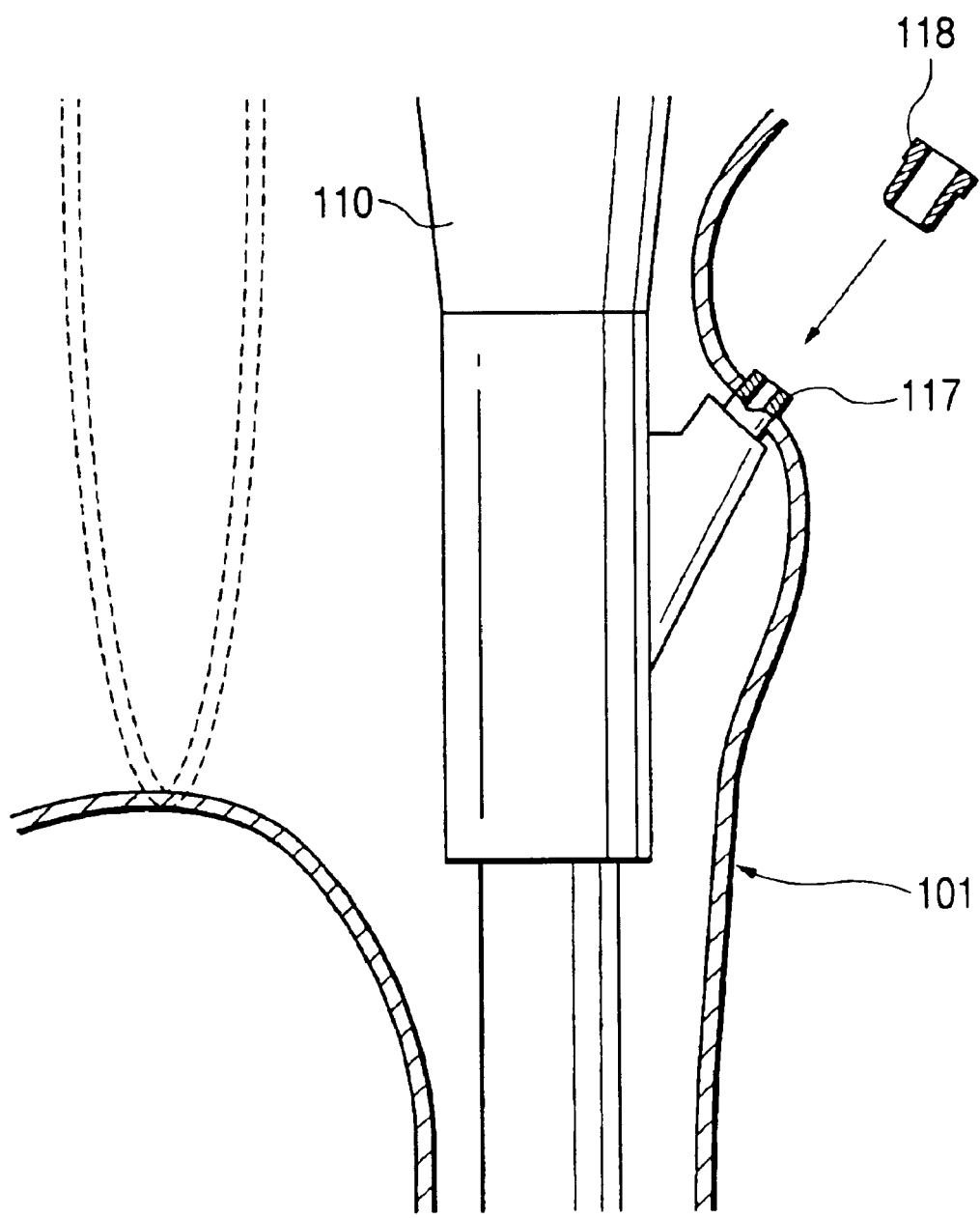
FIG. 6 is a partial sectional view of a state of covering a cover on an operating portion according to another modification of the first embodiment of the invention.

Further, as shown by FIG. 6, when a treating piece inserting cap 117 to be opened to the outer face or the like is present at the operating portion 110, the treating piece inserting cap 117 may be projected from a hole formed at the cover 101 and may be fixed to the cover 101 in watertight by a hold ring 118 or the like locked to the treating piece inserting cap 117 from the outer side.

Second Embodiment

A main feature of a cover for preventing contamination of an operating portion of an endoscope according to this embodiment is such that an annular or ring-like band is used to tighten the cover, formed by a flexible material to overlap the total of the operating portion, from the outer side in the direction of the axial position of the rear side of a bending operating member by the ring-like band. By this feature, contamination of the operating portion can firmly be prevented by enveloping the total of the operating portion of the endoscope along with the bending operating member. Further, when the endoscope is used, the bending operating member can firmly and easily be operated without undergoing considerable resistance from the cover by firmly taking up the bending operating member.

Other features and advantages of the cover according to this embodiment are readily understandable from the description directed to this embodiment and/or the description directed to other embodiments.

Figure 9:
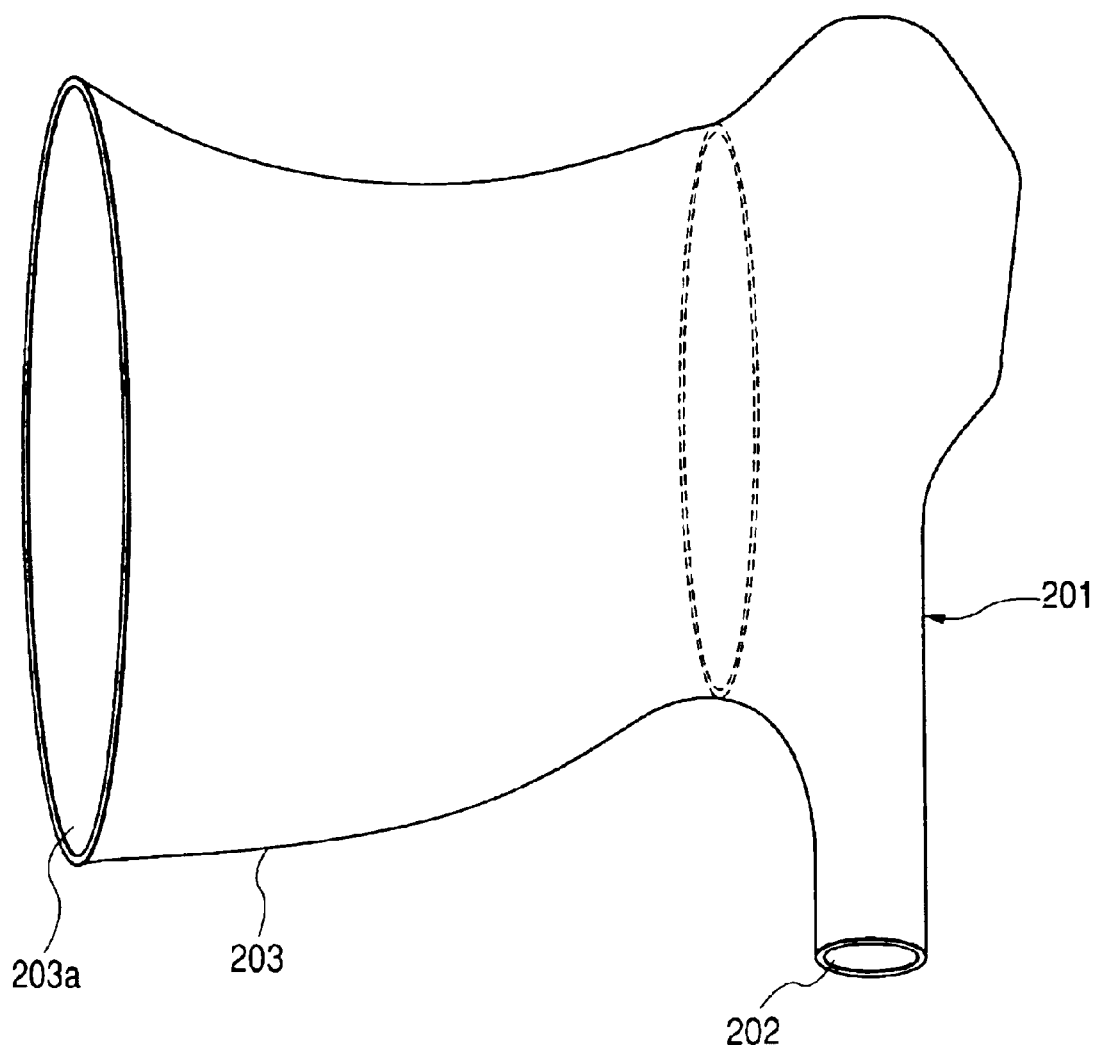
FIG. 9 is a side perspective view of a single member of a cover for preventing contamination of an operating portion according to the second embodiment of the invention.

FIG. 9 shows a single member of a cover 201 for preventing contamination of an operating portion of an endoscope. The cover 201 is formed in a bag-like shape enveloping a total of the operating portion of the endoscope, a lower end portion thereof is formed with a hole 202 for passing an inserting portion of the endoscope and a rear face thereof is formed with a sleeve-like portion 203 for inserting the hand to directly hold the operating portion. Notation 203a designates an opening portion of the sleeve-like portion 203.

As a material of the cover 201, a sheet of a flexible synthetic resin material of, for example, polyethylene, polypropylene or the like or a sheet of an elastic rubber material can be used.

Figure 10:
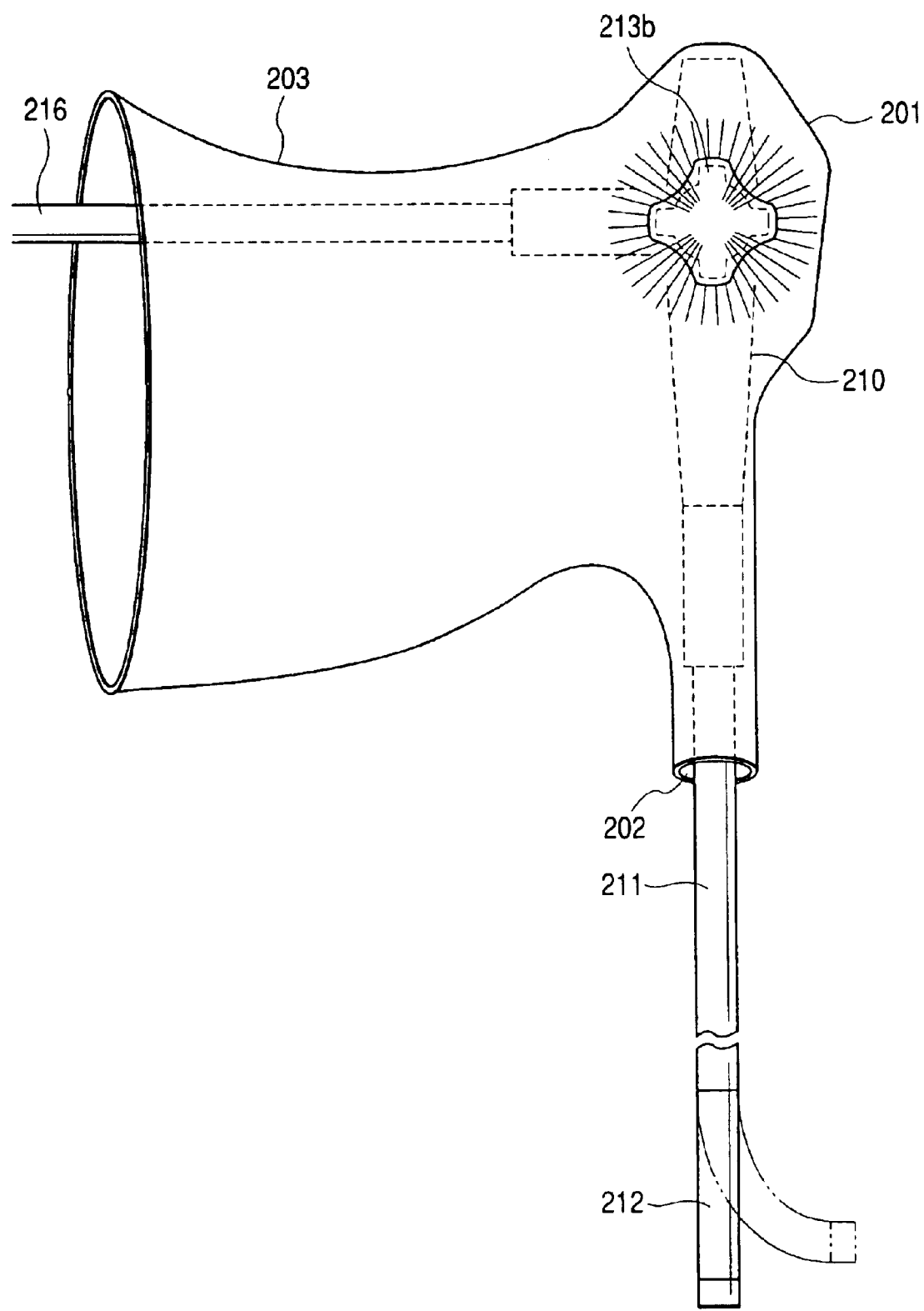
FIG. 10 is a side perspective view of a state of covering the cover on the operating portion according to the second embodiment of the invention.
Figure 11:
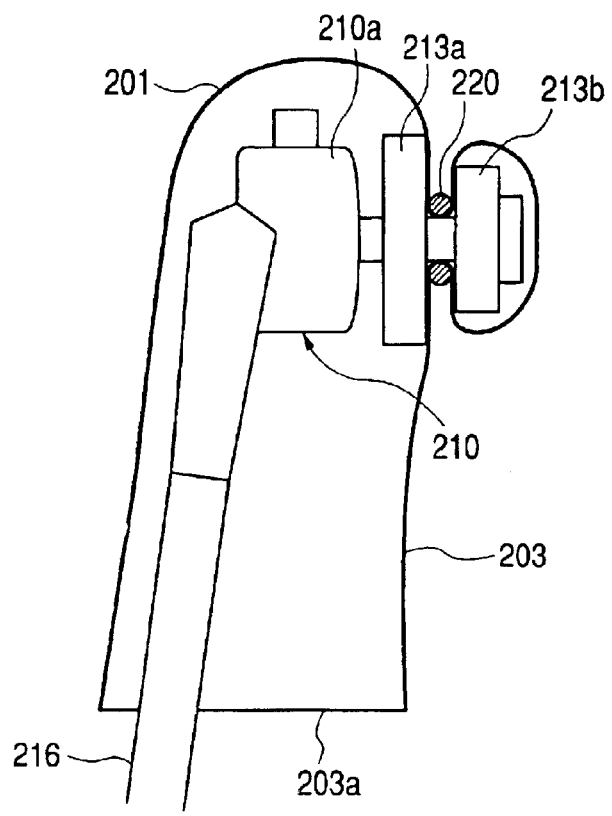
FIG. 11 is a plane perspective view of the state of covering the cover on the operating portion according to the second embodiment of the invention.

FIG. 10 shows a state of covering the cover 201 on the operating portion 210 of the endoscope. FIG. 11 is a plane perspective view thereof.

In the state, there is brought about a state in which the cover 201 entirely envelops a total of the operating portion 210 of the endoscope, a flexible tube 211 of the inserting portion of the endoscope is extended downwardly by passing the hole 202 and a light guide cable 216 is extended rearwardly from inside of the sleeve-like portion 203.

According to the endoscope, the operating portion 210 is connected to a base end of the flexible tube 211 of the inserting portion and by operating to rotate bending operating knobs 213a and 213b attached to a shaft member projected sideways from an operating portion body 210a around an axis, as shown by two-dotted chain lines in FIG. 10, a bending portion 212 provided at a front end portion of the flexible tube 211 of the inserting portion is bent.

The bending operating knobs 213a and 213b are arranged in a state in which the bending operating knob 213b for a left and right direction for bending the bending portion 212 in a left and right direction, is overlapped on an outer side of the bending operating knob 213a for an up and down direction for bending the bending portion 212 in an up and down direction on the same axis line.

Further, the cover 201 is brought into a state of being tightened from an outer side in a direction of an axial position of a rear side of the bending operating knob 213b for the left and right direction by an elastic ring-like band 220 made of, for example, rubber at a portion thereof covering the bending operating knobs 213a and 213b. The expandable and contractable ring-like band 220 is attachable and detachable to and from the portion and the ring-like band 220 is attached after the cover 201 has been covered on the operating portion 210.

In this way, by bringing the cover 1 into the state of being tightened on the rear side of the bending operating knob 213b for the left and right direction, the cover 201 is formed into a shape along a contour of the bending operating knob 213b for the left and right direction at a portion thereof surrounding the bending operating knob 213b for the left and right direction.

Further, as shown by FIG. 10, a number of wrinkles are produced radially in a direction of a center of the bending operating knob 213b for the left and right direction and even when the cover 201 enveloping the portion is rotated along with the bending operating knob 213b for the left and right direction, only the wrinkles are stretched and the cover 201 can be rotated without considerable resistance.

Figure 7:
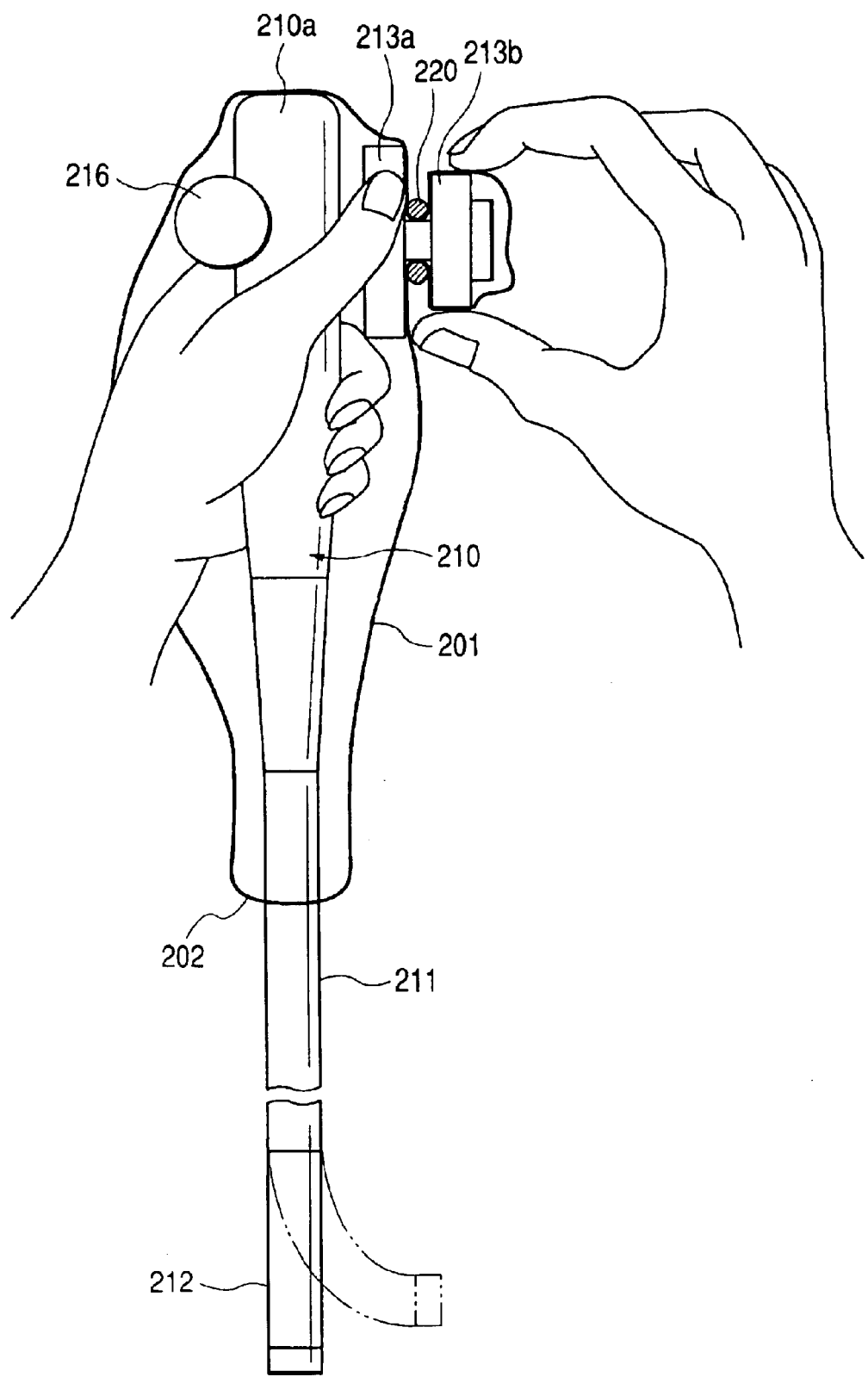
FIG. 7 is a rear perspective view of a state of using a second embodiment of the invention.
Figure 8:
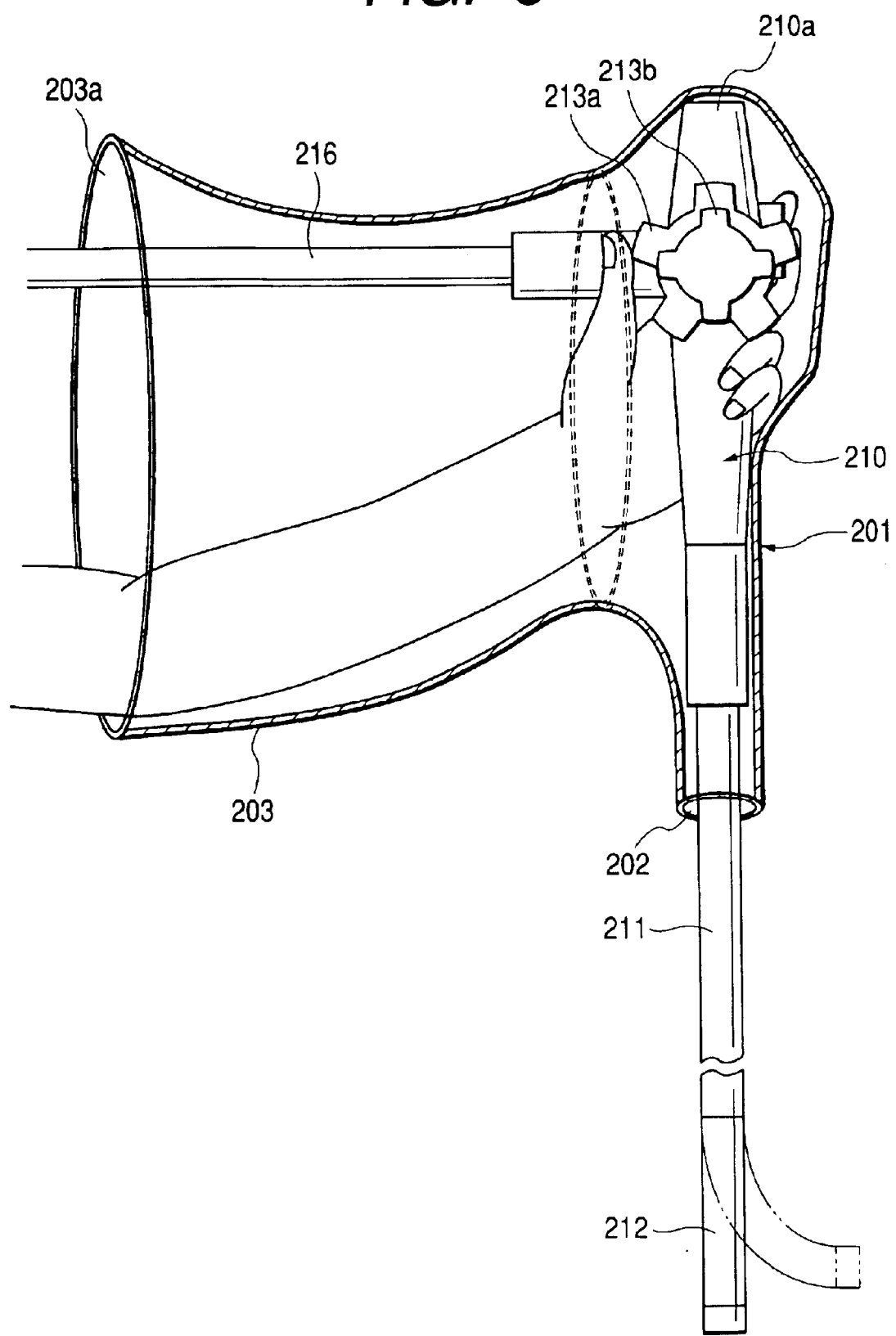
FIG. 8 is a side perspective view of the state of using the second embodiment of the invention.

FIG. 7 and FIG. 8 show a state of using the above-described embodiment, operation of rotating the bending operating knob 213a for the up and down direction is carried out on an inner side of the cover 201 by the fingers of the hand passed through the sleeve-like portion 203 for holding the operating portion 210 and operation of rotating the bending operating knob 213b for the left and right direction is carried out via the cover 201 from an outer side of the cover 201 as shown by FIG. 7.

As a result, not only the operation of the bending operating knob 213a for the up and down direction which is carried out on the inner side of the cover 201, can firmly and easily be carried out but also the operation of the bending operating knob 213b for the left and right direction which is carried out from the outer side of the cover 201, can firmly and easily be carried out without undergoing considerable resistance by firmly taking up the bending operating knob 213b for the left and right direction by the finger tips via the cover 201.

Further, the cover 201 entirely envelops the portions of the bending operating knobs 213a and 213b along with the body side of the operating portion without break and therefore, there is not a concern that the bending operating knobs 213a and 213b are contaminated or a dirty solution invades inside of the cover 201 from the portions of the bending operating knobs 213a and 213b.

Figure 12:
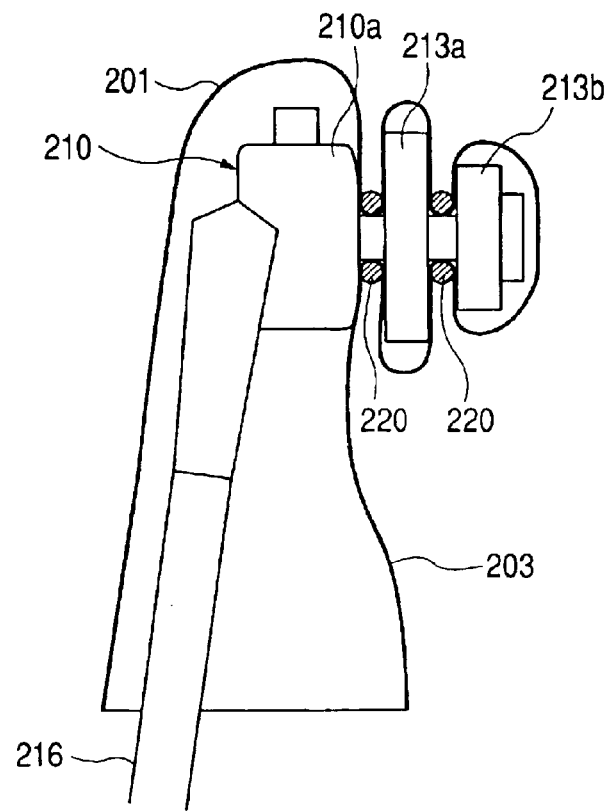
FIG. 12 is a plane perspective view of a state of covering the cover of an operating portion according to a modification of the second embodiment of the invention.
Figure 13:
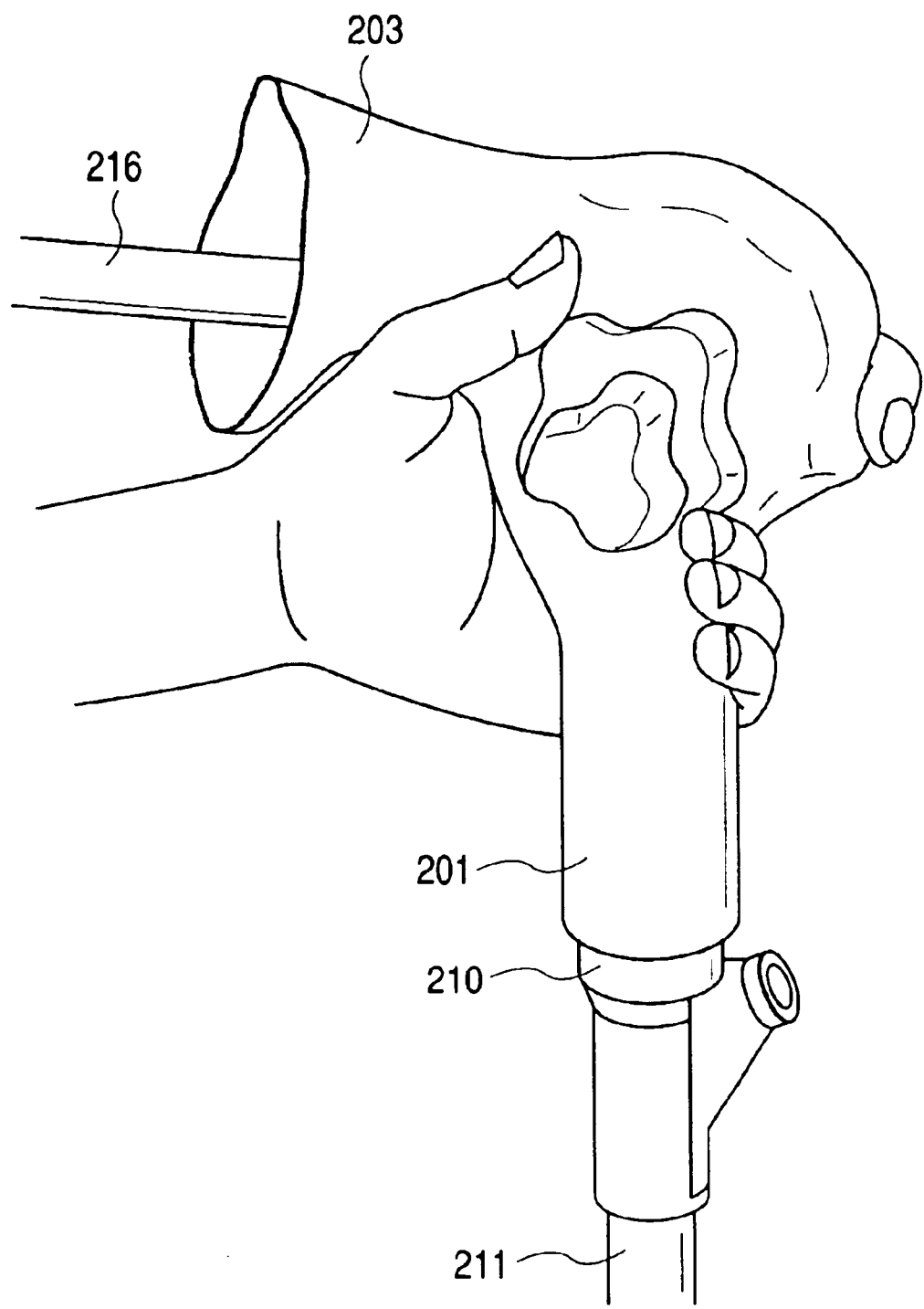
FIG. 13 is a perspective view of a state of using the modification of the second embodiment of the invention.

FIG. 12 is a plane perspective view of a state in which the cover 201 is covered on the operating portion 210 according to a modification of the second embodiment of the invention and FIG. 13 is a perspective view of a state of using this modification of the second embodiment.

According to this modification, the sleeve-like portion 203 is formed slenderly to pass only the light guide cable 216 and the operator holds the operating portion 210 from the outer side of the cover 201.

Then, also with regard to the portion of the bending operating knob 213a for the up and down direction, similar to the portion of the bending operating knob 213b for the left and right direction, the cover 201 is tightened from the outer side in a direction of an axial position on a rear side by the ring-like band 220 and the two bending operating knobs 213a and 213b can firmly and easily be operated to rotate from the outer side of the cover 201.

Third Embodiment

A main feature of a cover for preventing contamination of an operating portion of an endoscope according to this embodiment is such that a cylindrical portion enveloping a bending operating member is arranged in the state of being folded in a bellows-like shape at the space between the bending operating member and a surface of the operating portion body. By this feature, in accordance with the bending operation, the bellows-like shape portion of the cylindrical portion is brought into a state of being twisted and therefore, the bending operation can be carried out smoothly without generating so much resistance force.

Other features and advantages of the cover according to this embodiment are readily understandable from the description directed to this embodiment and/or the description directed to other embodiments.

Figure 16:
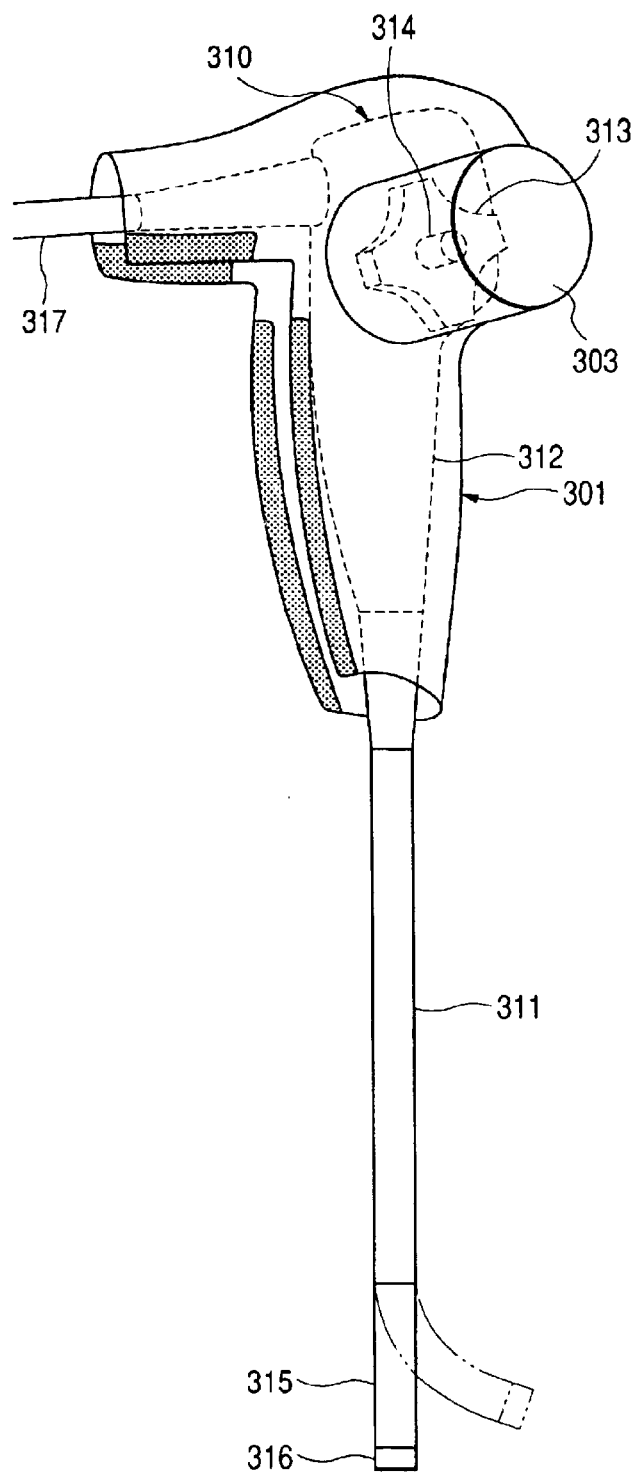
FIG. 16 is a perspective view of a state in the midst of covering the cover on the operating portion according to the third embodiment of the invention.

FIG. 15 shows a single member of a cover 301 for preventing contamination of an operating portion of an endoscope and FIG. 16 shows a state in which an operating portion 310 of the endoscope is put into the cover 301.

According to the endoscope, the operating portion 310 is connected to a base end of a flexible tube 311 of an inserting portion and by operating to rotate a bending operating knob 313 attached to a shaft member 314 projected sideways from an operating portion body 312 around an axis, a bending portion 315 provided at a front end portion of the flexible tube 311 of the inserting portion can remotely be bent as shown by two-dotted chain lines.

A front end of the bending portion 315 is connected with a front end portion main body 316 arranged with an observing window and the like. Numeral 317 designates a light guide cable connected to a light source-apparatus, not illustrated, and extended rearwardly from the operating portion 310.

The cover 301 is formed by molding a thin and flexible material in a sheet-like shape constituting the material by, for example, polypropylene, polyethylene or polyethylene tetrafluoride resin or the like in conformity with a shape of the operating portion 310 such that a total of the operating portion 310 of the endoscope can be enveloped.

The cover 301 is formed in a shape opening a rear portion side thereof to facilitate to put into and out the operating portion 310 of the endoscope and an edge portion of the portion is attached with a pressure sensitive bonding agent 302 for fittedly closing an opening edge after enveloping the endoscope.

Figure 17:
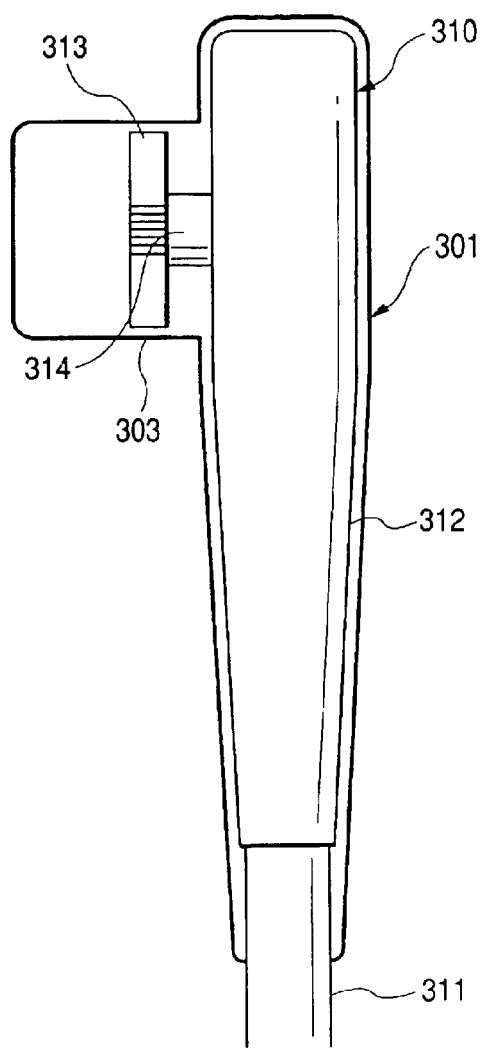
FIG. 17 is an outline front sectional view of the state in the midst of covering the cover on the operating portion according to the third embodiment of the invention.

Further, a portion 303 for enveloping the bending operating knob 313 of the cover 301, is formed to project sideways from the cover 301 in a shape of a cylinder a projected end portion of which is closed, and as shown by FIG. 17, an amount of projecting the cylindrical portion 303 from the cover 301 is set to be far larger than an amount of projecting the bending operating knob 313 from the operating portion body (for example, about twice)

Further, at a preparatory stage of using the endoscope, as shown by FIG. 14, by pushing to crush the cylindrical portion 303 in an axis line direction from an outer side, at a space at a surrounding of the shaft member 314 between the bending operating knob 313 and a surface of the operating portion body 312 contiguous thereto, the cylindrical portion 303 is brought into a state of being folded in a bellows-like shape. Notation 303a designates the bellows-like portion.

Figure 18:
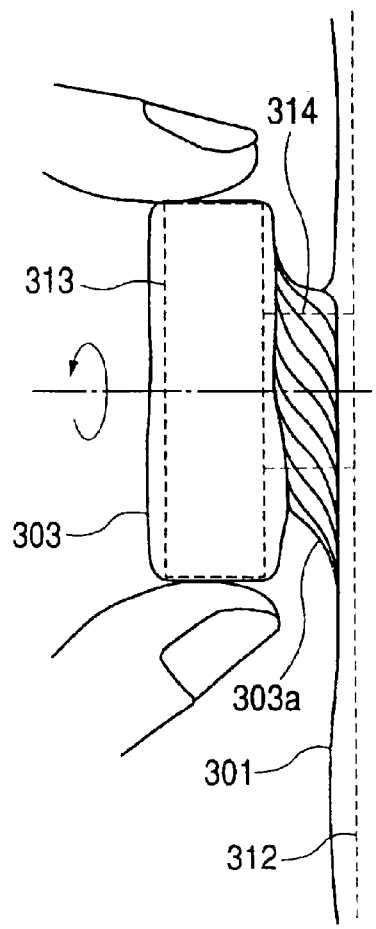
FIG. 18 is a partial front view of a bending operating state according to the third embodiment of the invention.

As a result, as shown by FIG. 18, in operating to rotate the bending operating knob 313, when the bending operating knob 313 is taken up and rotated from an outer side of the cylindrical portion 303 of the cover 301, the cylindrical portion 303 is twisted at the bellows-like portion 303a and therefore, the cylindrical portion 303 can smoothly be operated without generating so considerable resistance force.

Figure 19:
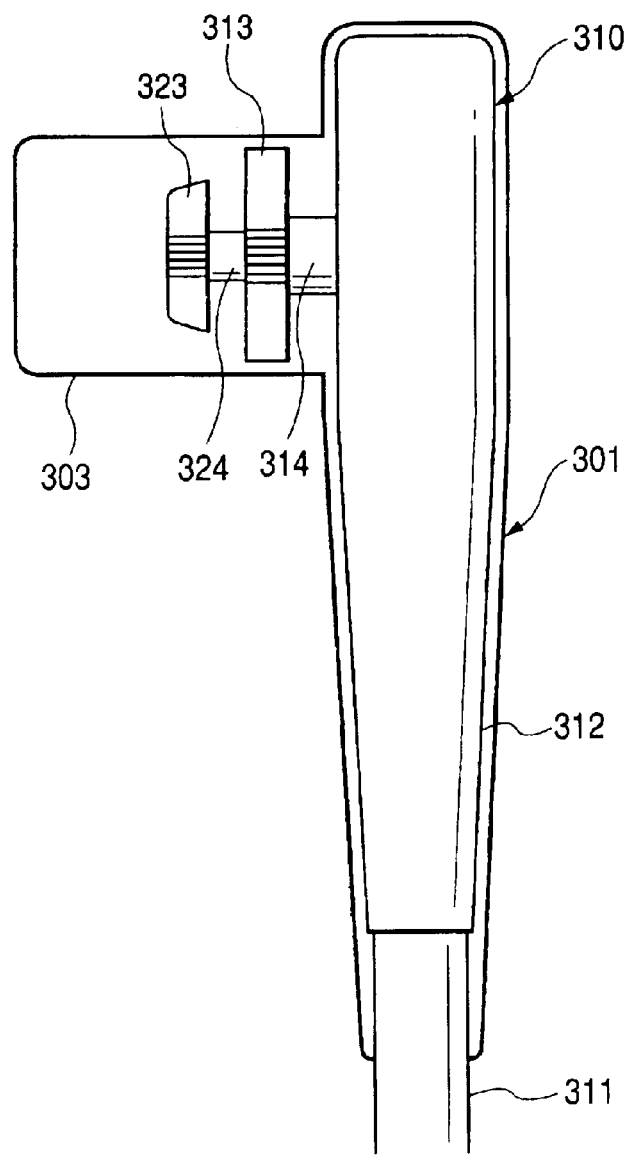
FIG. 19 is an outline front sectional view of a state in the midst of covering a cover on an operating portion according to a modification of the third embodiment of the invention.

Further, as shown by FIG. 19, when the bending operating knob 313 for an up and down direction and a bending operating knob 323 for a left and right direction, are arranged to shift positions thereof in the axis line direction to be operated to rotate independently from each other, the cylindrical portion 303 is formed to project higher than the two bending operating knobs 313 and 323.

Further, as shown by FIG. 20, by pushing to crush the cylindrical portion 303 in the axis line direction, the cylindrical portion 303 can be brought into a state of being folded in the bellows-like shape even at a portion between the two bending operating knobs 313 and 323 and the two bending operating knobs 313 and 323 can be operated to rotate respectively smoothly.

Further, the invention is not limited to the above-described embodiment but as shown by, for example, FIG. 21, a projected end 303b of the cylindrical-portion 303 may be enclosed in a linear shape. Further, the cover 301 may be formed in a bag-like shape by a highly elastic material to thereby dispense with the pressure sensitive bonding agent 302.

Fourth Embodiment

A main feature of a cover for preventing contamination of an operating portion of an endoscope according to this embodiment is such that a cap fixing member is provided for fixing the cover and a cap in a state in which the end portion opening of the cap arranged at the operating portion is projected to the outer side of the cover to be communicated and connected to a path opened at a front end of an inserting portion of the endoscope. By this feature, the end portion opening of the cap is disposed outside of the cover in the state of use and therefore, the cover for preventing contamination of the operating portion of the endoscope according to this embodiment is hygienically highly safe with no concern of contaminating the operating portion even when a dirty solution is leaked from the cap.

Other features and advantages of the cover according to this embodiment are readily understandable from the description directed to this embodiment and/or the description directed to other embodiments.

Figure 22:
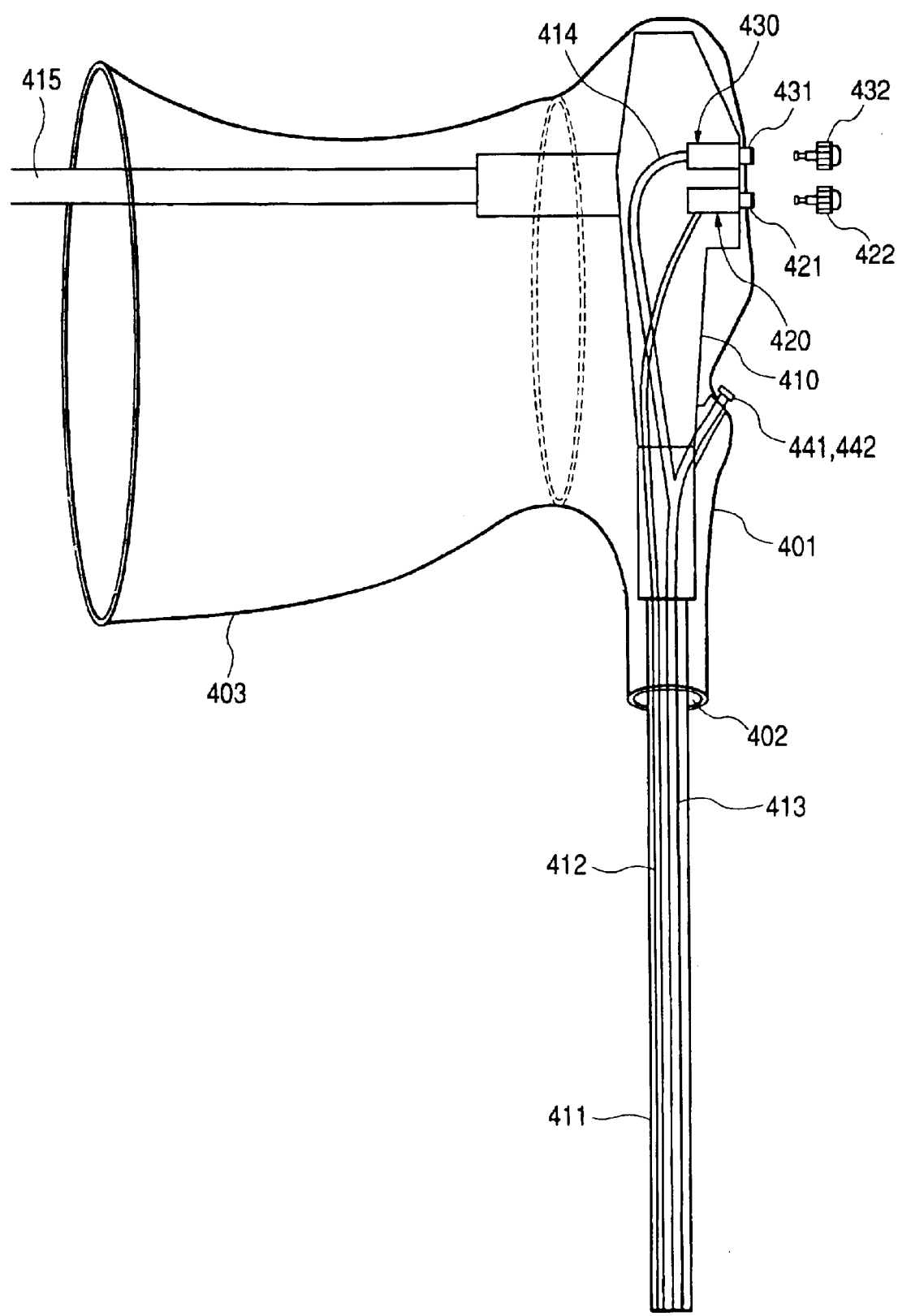
FIG. 22 is a side perspective view showing a total constitution of a preparatory state of use in which a cover is covered on an operating portion of an endoscope according to a fourth embodiment of the invention.

FIG. 22 shows a preparatory state of use in which a cover 401 is covered on an operating portion 410 of an endoscope.

At inside of an inserting portion 411 connected to a lower end of the operating portion 410, an air feed and water feed path 412 and a treating piece inserting channel 413 and the like are arranged to insert and front end openings thereof are arranged at a front end of the inserting portion 411.

At a front face of an upper half of the operating portion 410, an air feed and water feed operating valve 420 and a suction operating valve 430 are arranged to align, a base end of the air feed and water feed path 412 is communicated and connected to the air feed and water feed operating valve 420 and a suction tube 414 branched from the treating piece inserting channel 413 is communicated and connected to the suction operating valve 430.

Both of the air feed and water feed operating valve 420 and the suction operating valve 430 are constituted by attachably and detachably attaching switching member units 422 and 432 (cap fixing members) in a shape of a piston to caps 421 and 431 in a shape of a cylinder connected with the paths (air feed and water feed path 412, suction tube 414) from sides of end portion openings thereof.

Further, a base end of the treating piece inserting channel 413 is arranged on a lower side of the operating portion 410 and a treating piece inserting cap 441 is provided at the inlet portion thereof, is attachably and detachably attached with a forceps plug 442 from a side of an end portion opening thereof. Further, although paths for connecting the air feed and water feed operating valve 420 and the suction operating valve 430 and outside air feed and water feed apparatus and suction apparatus, are arranged to insert into a light guide cable 415, illustration thereof is omitted.

The cover 401 is formed to be covered entirely on the operating portion 410, a lower end portion thereof is formed with a hole 402 for passing the inserting portion 411 and a rear face side thereof is formed with a sleeve-like portion 403 for inserting the light guide cable 415.

Further, although according to the embodiment, the operating portion 410 can directly be gripped to hold at inside of the cover 401 bypassing the arm of the operator through the sleeve-like portion 403, the operating portion 410 may be gripped from an outer side of the cover by forming the sleeve-like portion 403 slenderly.

Figure 23:
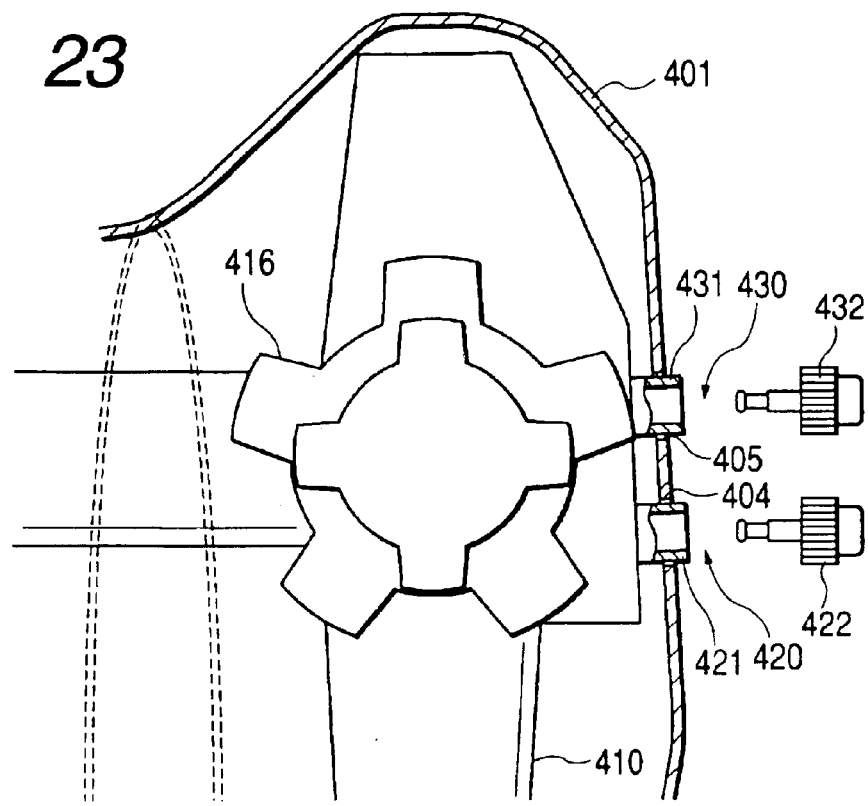
FIG. 23 is a partial side perspective view of the preparatory state of use at a vicinity of an operating valve in which the cover is covered on the operating portion of the endoscope according to the fourth embodiment of the invention.

FIG. 23 shows portions of the air feed and water feed operating valve 420 and suction operating valve 430 and numeral 416 designates a bending operating knob projected from a side face of the operating portion 410. The cover 401 is bored with holes 404 and 405 having sizes for respectively passing the cap 421 of the air feed and water feed operating valve 420 and the cap 431 of the suction operating valve 430 and the path switching member units 422 and 432 are attached to and detached from the caps 421 and 431 from the outer side of the cover 401.

Figure 24:
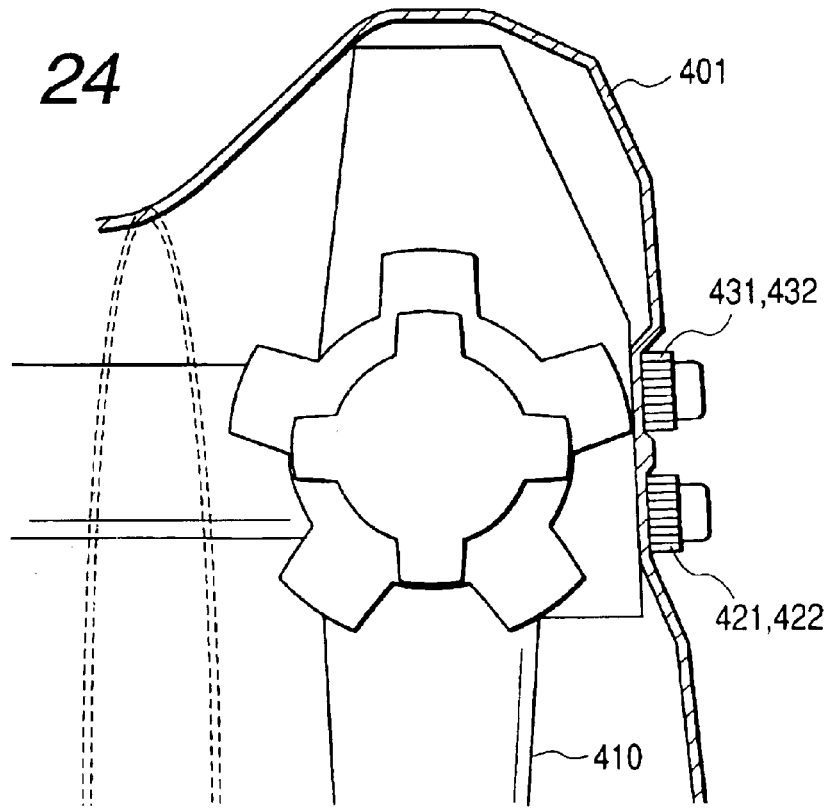
FIG. 24 is a partial side perspective view of a state of use at a vicinity of the operating portion in which the cover is covered on the operating portion of the endoscope according to the fourth embodiment of the invention.

Further, as shown by FIG. 24, when the path switching member units 422 and 432 are attached to the caps 421 and 431 by, for example, screwing from the outer side of the cover 401, by large diameter portions of the path switching member units 422 and 432, the cover 401 is pressed to a surface of the operating portion 410 and there is brought about a state of fixing the cover 401 and the caps 421 and 431 in a state of projecting end portion openings of the caps 421 and 431 to the outer side of the cover 431. Further, portions of the cover 401 at the holes 404 and 405 are brought into an enclosed state by pushing to crush edge portions thereof over an entire periphery thereof.

As a result, in a state of using the endoscope, the caps 421 and 431 are brought into a state of opening to an outer face of the cover 401 and therefore, even when a dirty solution is leaked out from the end portion openings of the caps 421 and 431, the operating portion 410 at inside of the cover 401 is not contaminated.

Figure 25:
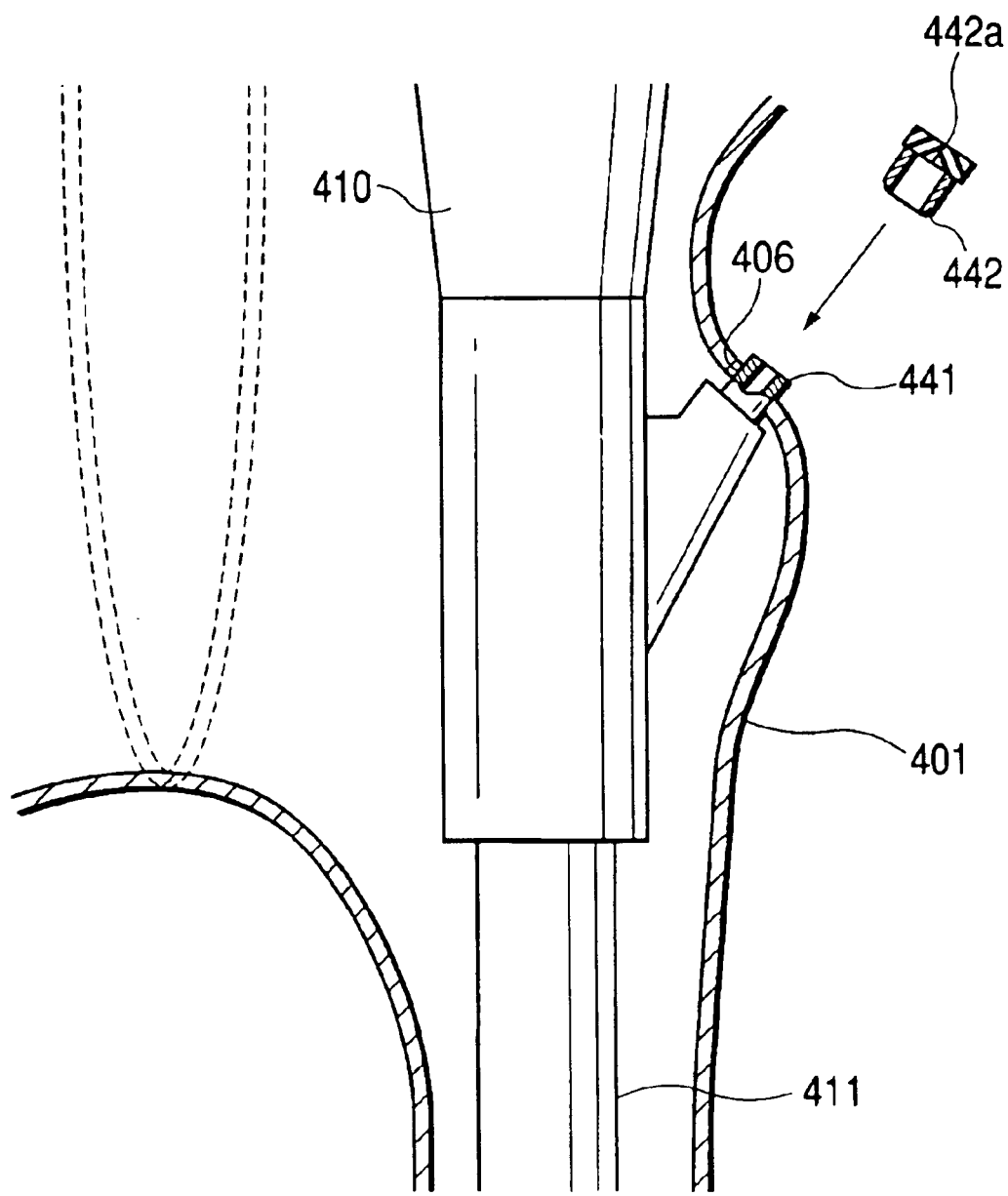
FIG. 25 is a partial side perspective view of a preparatory state of use at a vicinity of a treating piece inserting portion in which the cover is covered on the operating portion of the endoscope according to the fourth embodiment of the invention.

FIG. 25 shows a portion of the treating piece inserting cap 441 and a slit 442a is formed at an elastic closing film made of rubber provided at the forceps plug 442. The cover 401 is formed with a hole 406 having a size of passing the treating piece inserting cap 441 and the forceps plug 442 is attached to and detached from the treating piece inserting cap 441 from the outer side of the cover 401.

Figure 26:
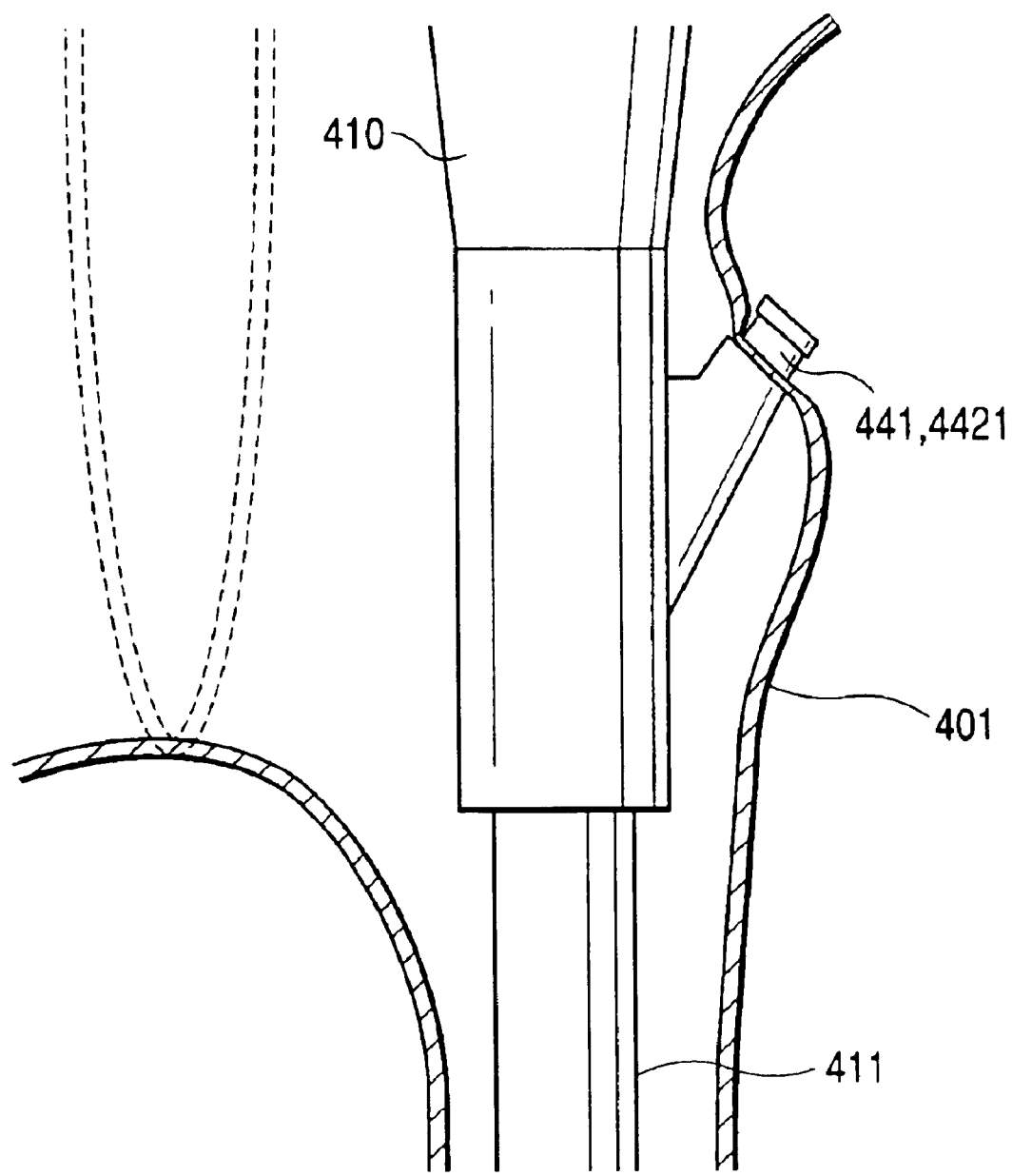
FIG. 26 is a partial side perspective view of a state of use at the vicinity of the treating piece inserting portion in which the cover is covered on the operating portion of the endoscope according to the fourth embodiment of the invention.

Further, as shown by FIG. 26, when the forceps plug 442 is attached to the treating piece inserting cap 441 by, for example, screwing from the outer side of the cover 401, the cover 401 is pressed to the surface of the operating portion 410 by the forceps plug 442 and the cover 401 and the treating piece inserting cap 441 are brought into a fixed state in a state in which the end portion opening of the treating piece inserting cap 441 is projected to the outer side of the cover 401.

As a result, in a state of using the endoscope, the treating piece inserting cap 441 is brought into a state of opening to the outer face of the cover 401 and therefore, even when a dirty solution is leaked out from the end portion opening of the treating piece inserting cap 441, the operating portion 410 at inside of the cover 401 is not contaminated.

Figure 27:
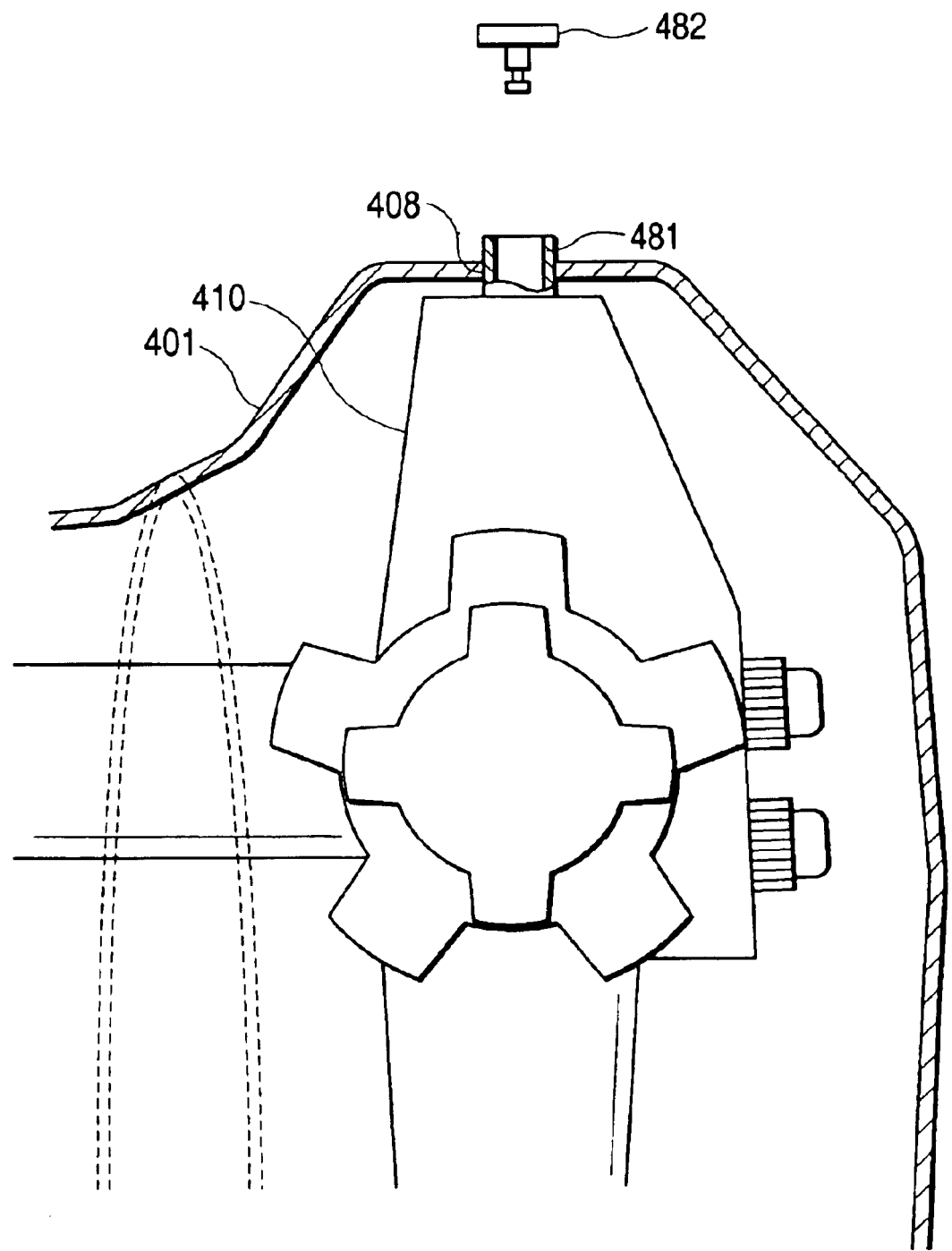
FIG. 27 is a partial side perspective view of a preparatory state of use according to a modification of the fourth embodiment of the invention.

Further, the invention is not limited to the above-described embodiment but, for example, as shown by FIG. 27, the invention is applicable even in the case in which a cap 481 communicated and connected to a path (for example auxiliary water feed tube) opened to a front end portion of the inserting portion 411, is disposed at a head portion of the operating portion 410. Numeral 482 designates a lid member attached to and detached from the cap 481 from the outer side of the cover 401.

Fifth Embodiment

A main feature of a cover for preventing contamination of an operating portion of an endoscope according to this embodiment is such that a rear portion and a lower portion are continuously formed to open serially, other portion is formed in a bag-like shape loosely surrounding the operating portion, an edge portion shape maintaining member for maintaining a shape of a portion along an opening edge portion of the rear portion to the degree of not deforming the shape, is arranged and at the lower half portion of the rear portion, an openable and closable closed state maintaining member capable of maintaining the portion in the closed state, is arranged. By this feature, the operator can operate the operating portion by directly gripping and stably holding the operating portion without hindrance by inserting the hand from the upper half portion of the rear portion into the cover for preventing contamination of the operating portion of the endoscope. The hand on the side of holding the operating portion is not contaminated even in carrying out the inspection by the endoscope and therefore, operation after inspection or the like can hygienically be carried out with no hindrance without contaminating the surrounding.

Other features and advantages of the cover according to this embodiment are readily understandable from the description directed to this embodiment and/or the description directed to other embodiments.

Figure 29:
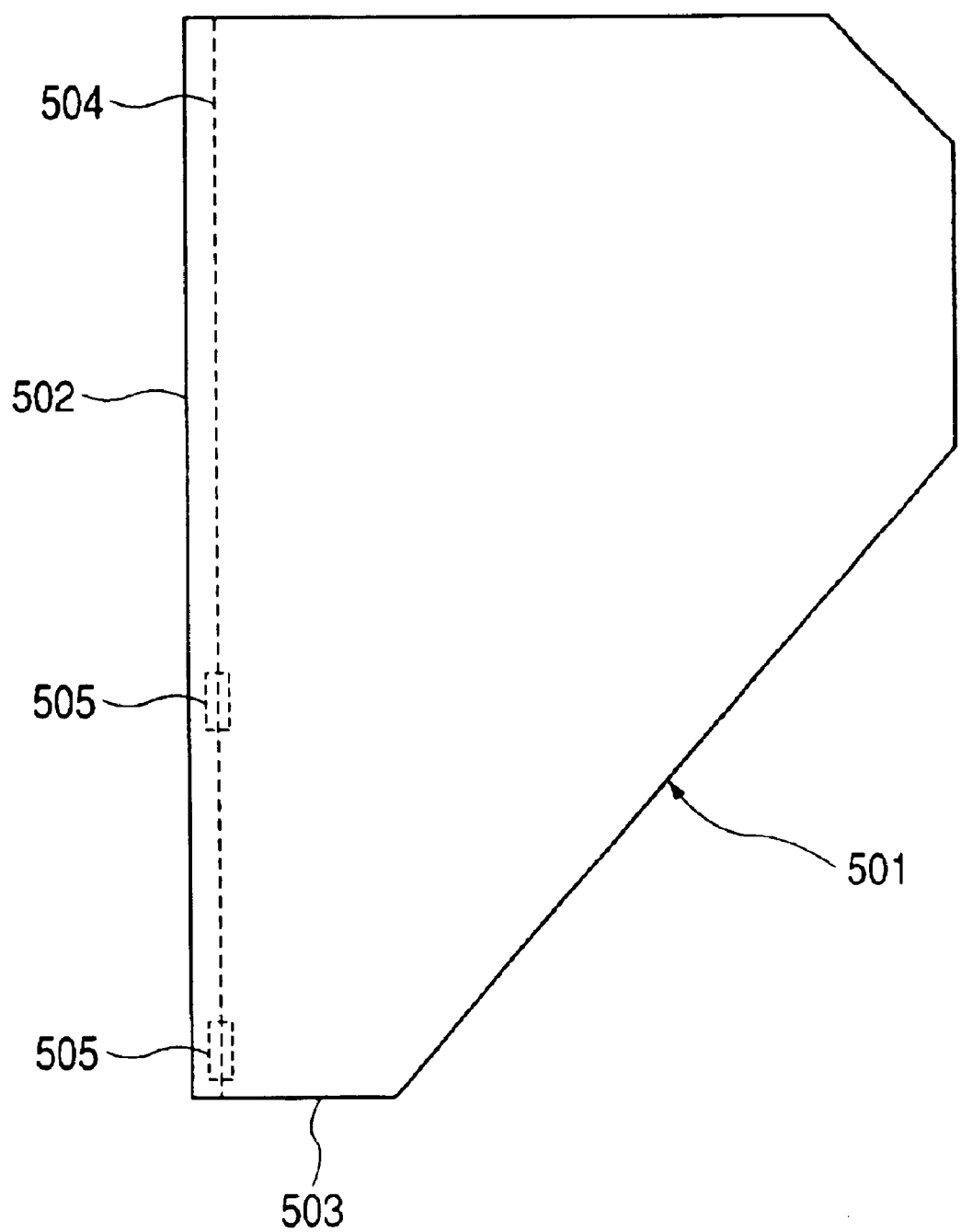
FIG. 29 is a side view of the cover for preventing contamination of the operating portion of the endoscope according to the fifth embodiment of the invention.
Figure 30:
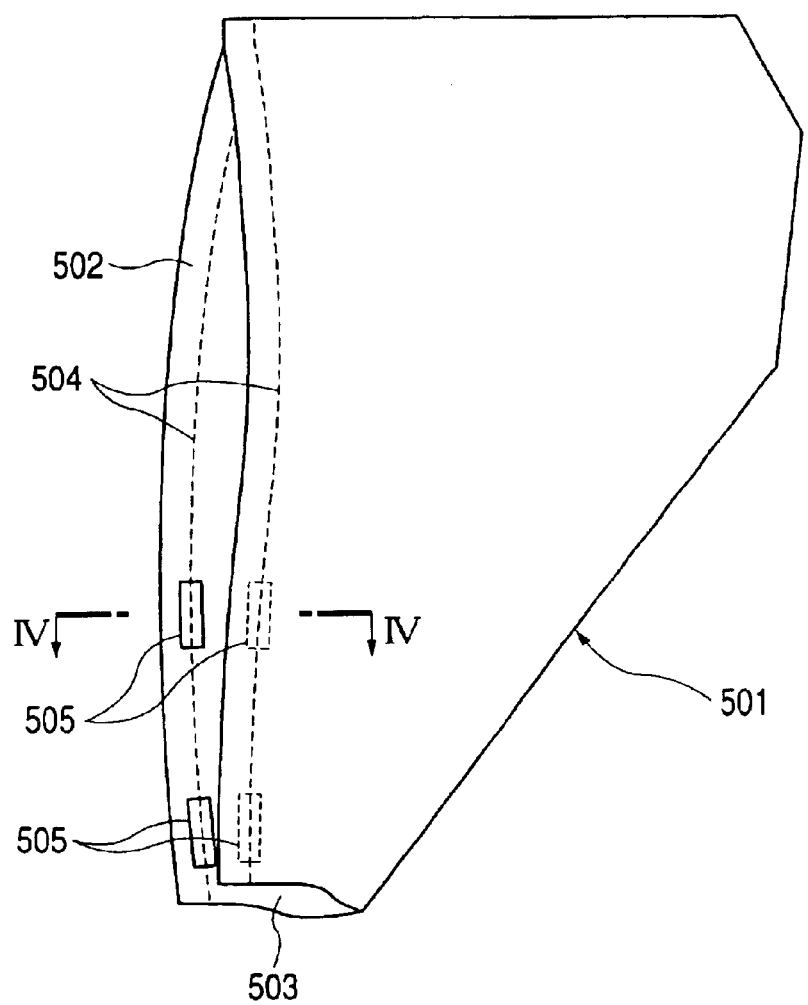
FIG. 30 is a perspective view of the cover for preventing contamination of the operating portion of the endoscope according to the fifth embodiment of the invention.

FIG. 29 and FIG. 30 show a cover 501 for preventing contamination of an operating portion according to a fifth embodiment of the invention, FIG. 29 is a side view and FIG. 30 is a perspective view.

The cover 501 for preventing contamination of an operating portion is formed in a bag-like shape capable of loosely covering a total of an operating portion 512 of an endoscope 510, a rear portion 512 and a lower portion 503 thereof are continuously formed to open serially and other portion is formed into a holeless bag-like shape loosely surrounding the operating portion 512.

As a material of the cover 501 for preventing contamination of the operating portion, a seat or the like of a flexible synthetic resin material of, for example, polyethylene, polypropylene or an elastic rubber material can be used and although a shape of the bag-like portion may be angular to some degree as in the embodiment, the shape may be a rounded shape.

Further, the rear portion 502 of the cover 501 for preventing contamination of the operating portion is provided with a length of substantially a total length of the operating portion 512 (for example, about 15 through 20 cm) and the lower portion is formed by a length to a degree of loosely passing an inserting portion 511, (for example, about 2 through 3 cm).

The cover 501 for preventing contamination of the operating portion is formed by welding two sheets of thin sheets having the same shape at a total edge portion other than those of the rear portion 502 and the lower portion 503. However, the cover 501 may be formed by any method such as using a material formed in a bag-like shape.

An edge portion shape maintaining member 504 is attached along an opening edge portion of the rear portion 502 of the cover 501 for preventing contamination of the operating portion for maintaining a shape of the portion. The edge portion shape maintaining member 504 according to the embodiment is, for example, a wire made of a metal discontinuously attached along the opening edge portion of the rear portion 503 and the shape of the opening edge portion of the rear portion 502, the shape of which is crumpled and is not maintained at all when the edge portion shape maintaining member 504 is not present, is maintained by the edge portion shape maintaining member 504 to a degree of not being deformed totally.

However, since the edge portion shape maintaining member 504 is discontinuously arranged, the shape of the opening edge portion of the rear portion 502 can easily be deformed when exerted with external force. Further, when an elastic plastic material or the like is used as the edge shape maintaining member 504, even one piece of a serial wire or a strip-like member functions similar to the edge shape maintaining member 504 according to the embodiment.

At a lower half portion of the rear portion 502 of the cover 501 for preventing contamination of the operating portion, an openable and closable closed state maintaining member 505 is provided at a vicinity of the opening edge portion.

Figure 31:
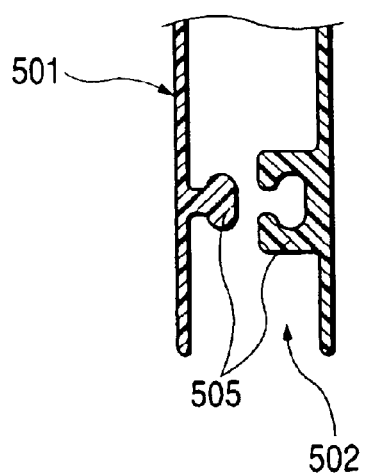
FIG. 31 is a sectional view taken along a line IV—IV in FIG. 30 of the cover for preventing contamination of the operating portion of the endoscope according to the fifth embodiment of the invention.
Figure 32:
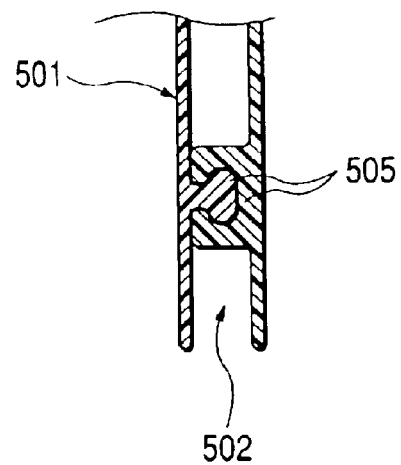
FIG. 32 is a sectional-view of a state in which a closed state maintaining member shown in FIG. 31 of the cover for preventing contamination of the operating portion of the endoscope according to the fifth embodiment of the invention is set to a closed state.

As shown by FIG. 31 illustrating a section taken along a line IV—IV in FIG. 30, the closed state maintaining member 505 of the embodiment is a slender hook-like member comprising a projected member and a recessed member attachable and detachable to and from each other and by engaging the members as shown by FIG. 32, the lower half portion of the rear portion 502 is maintained in a closed state.

Further, although according to the embodiment, the closed state maintaining members 505 are arranged at two locations of a lower end portion and a vicinity of a center of the rear portion 502, other arrangement or number of pieces thereof may be used. Further, as the closed state maintaining member 505, plane fasteners of so-to-speak magic tape (registered trade mark) or the like or other means may be used.

Figure 33:
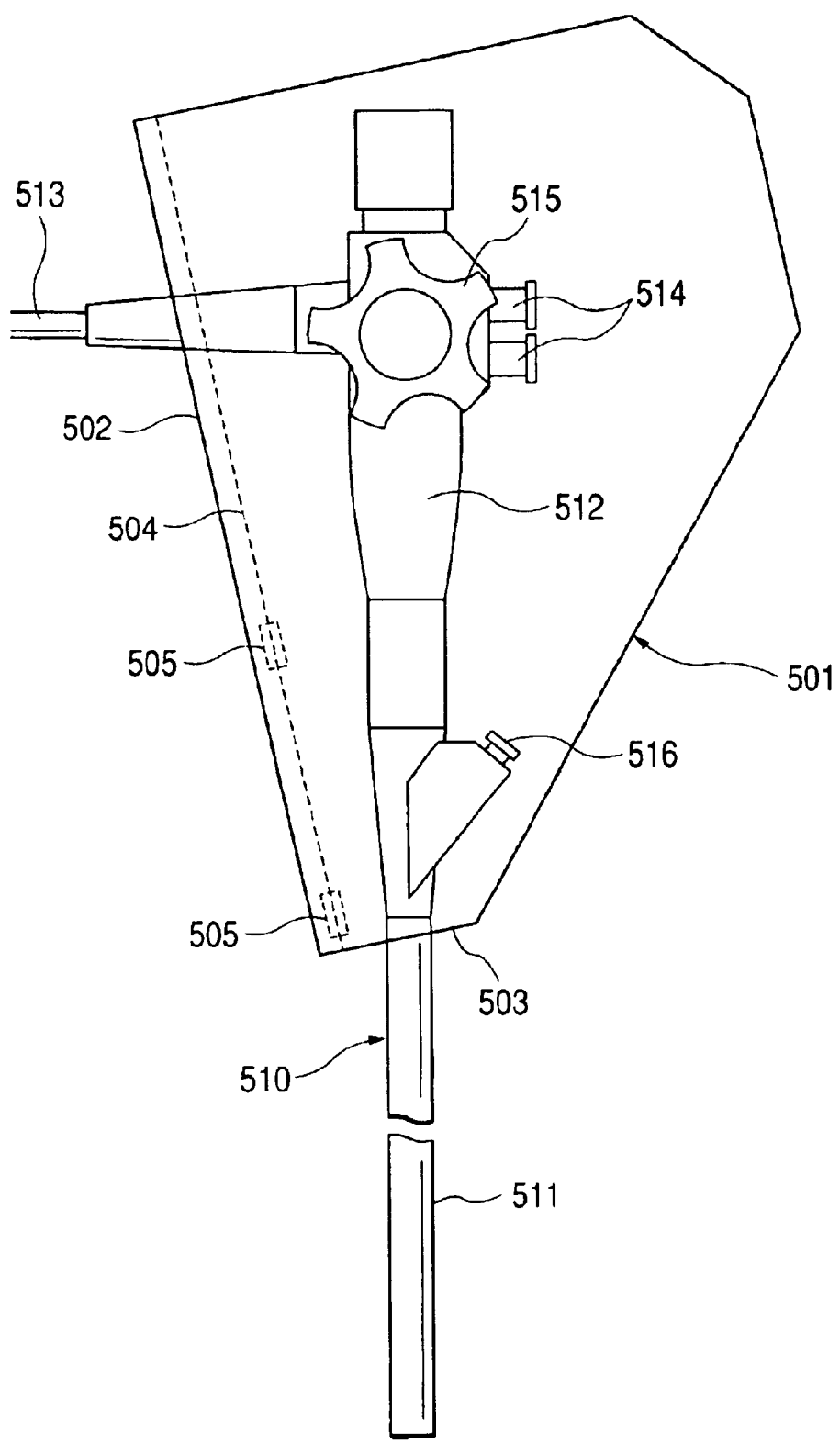
FIG. 33 is a perspective view of a state in which the cover for preventing contamination of the operating portion of the endoscope according to the fifth embodiment of the invention is covered on the operating portion.

FIG. 33 is a perspective view showing a state of covering the cover 501 for preventing contamination of the operating portion according to the embodiment on the operating portion 512 of the endoscope 510. The endoscope 510 is constructed by a constitution in which a lower end of the operating portion 512 is connected with a base end of the inserting portion 511 in a shape of a flexible tube, a base end of a light guide cable 513 is connected to a vicinity of an upper end of a rear face thereof, an operating button 514 for carrying out operation of air feed and water feed and suction is arranged at an upper portion of a front face thereof and a bending operating knob 515 is arranged at aside face thereof. Numeral 516 designates a treating piece inserting cap.

Since the rear portion 502 and the lower portion 503 are continuously formed to open serially, the cover 501 for preventing contamination of the operating portion can be brought into a covered state as shown by FIG. 33 by only opening the portion and covering the cover 501 on the operating portion 512 from a front side.

Further, by closing the closed state maintaining member 505 in a state of passing the inserting portion 511 through the lower portion 503 and passing the light guide cable 513 through the upper half portion of the rear portion 502, the cover 501 for preventing contamination of the operating portion is set to a state of loosely covering the operating portion 512.

Figure 28:
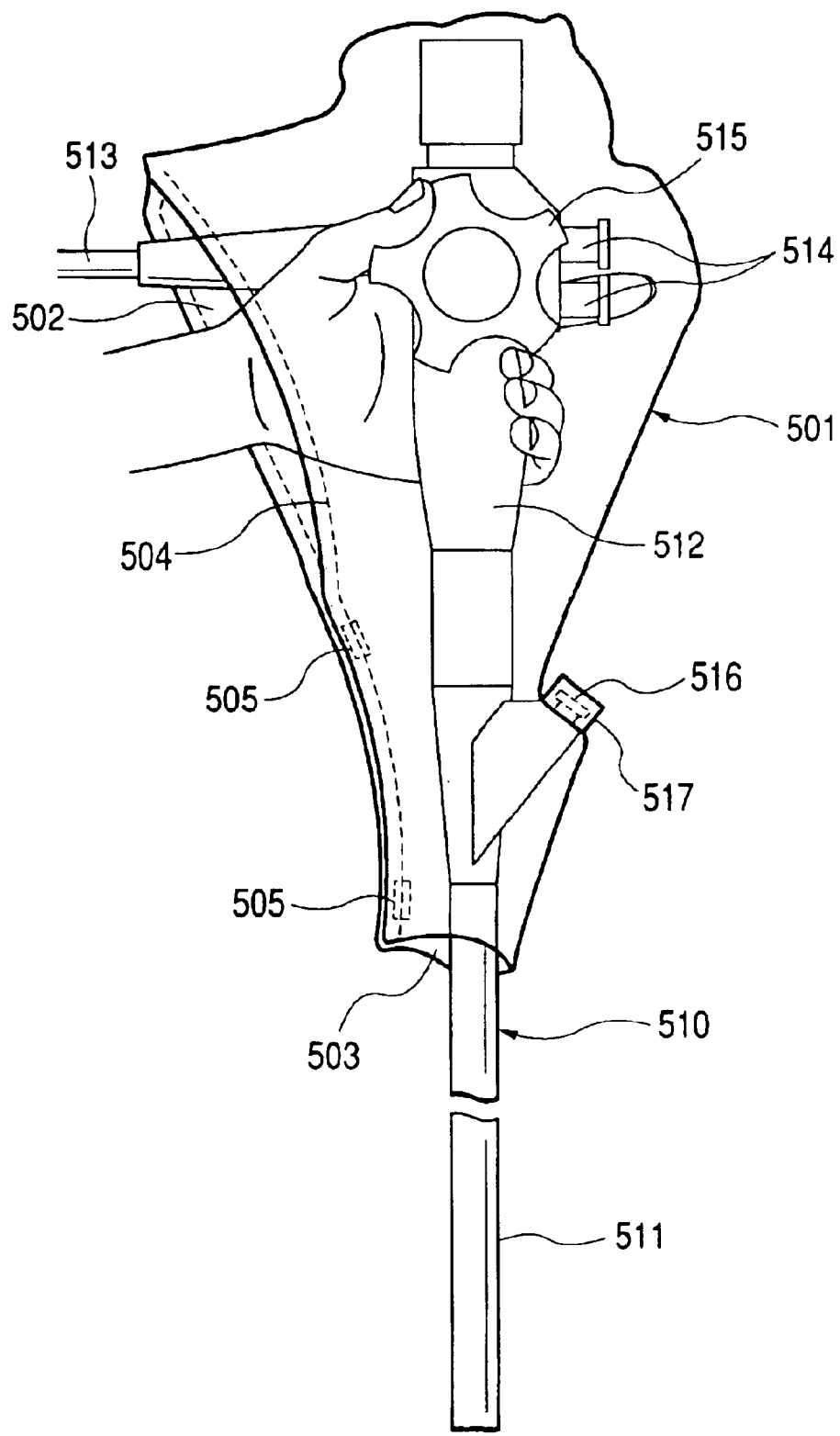
FIG. 28 is a perspective view of a state of use in which a cover for preventing contamination of an operating portion of an endoscope according to a fifth embodiment of the invention is covered on the operating portion.

Next, as shown by FIG. 28, by penetrating the treating piece inserting cap 516 through the cover 1 for preventing contamination of the operating portion and engaging a cover holding member 517 to the treating piece inserting cap 516 from an outer side, the cover 501 for preventing contamination of the operating portion is brought into a state of being fixed to the portion of the treating piece inserting cap 516.

The upper half portion of the rear portion 502 of the cover 501 for preventing contamination of the operating portion is passed with only the light guide cable 513 and is widely opened. Therefore, the operator can directly grip to hold the operating portion 512 by inserting the hand into the cover 501 for preventing contamination of the operating portion.

In the state, the operator grips a lower half portion of the operating portion 512 and at the same time, carries out operation of depressing the operating-button 514 projected to the front side of the operating portion 512, operation of rotating the bending operating knob 515 projected from a side face of the operating portion 512 at inside of the cover 501 for preventing contamination of the operating portion and the cover 501 for preventing contamination of the operating portion is loosely covered from the operating portion 512 to a degree of not hindering the operation.

In this way, the operator can directly hold the operating portion 512 at inside of the cover 501 for preventing contamination of the operating portion and can carry out inspection by the endoscope without contaminating the hand on the side of holding the operating portion 512.

Figure 34:
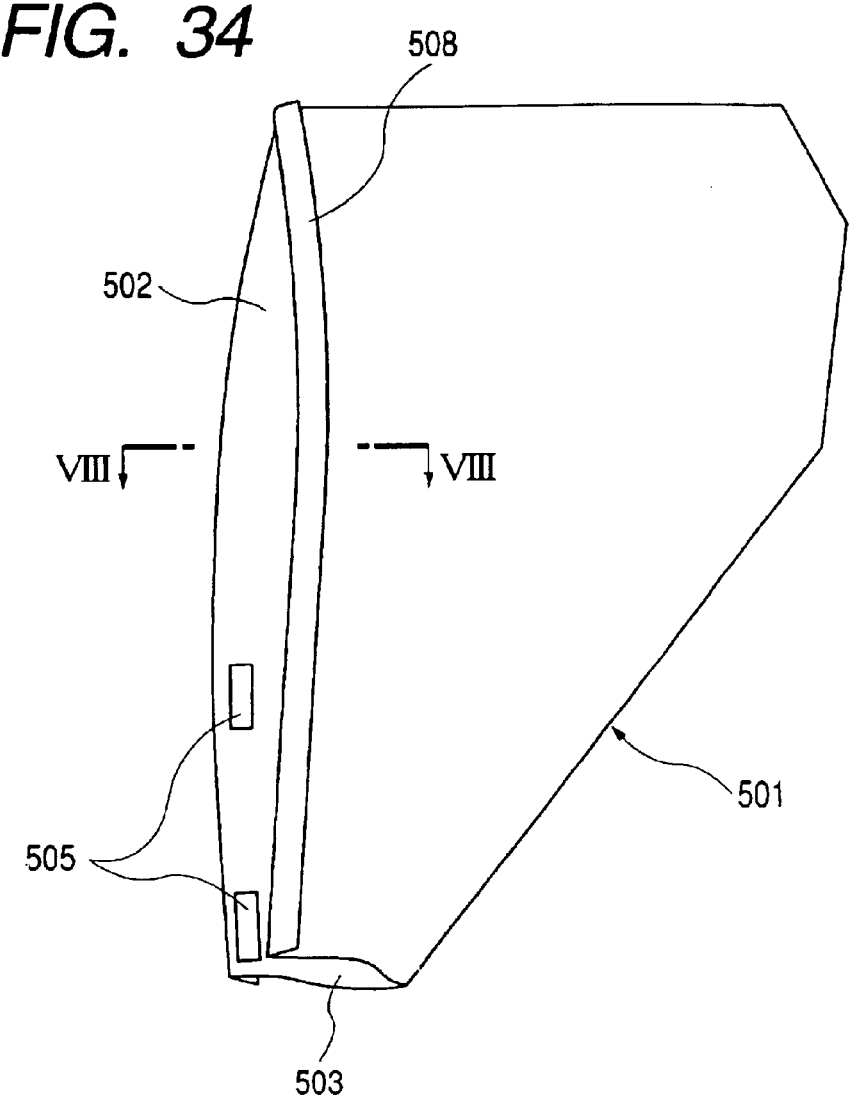
FIG. 34 is a perspective view of a cover for preventing contamination of an operating portion of an endoscope according to a modification of the fifth embodiment of the invention.

FIG. 34 shows the cover 501 for preventing contamination of the operating portion according to a modification of the fifth embodiment of the invention added with a trough-like member 508 for restricting a dirty solution (5100) adhered to an outer surface of the cover 501 for preventing contamination of the operating portion from flowing from the opening edge portion to an inner side along the outer surface side of the opening edge portion of the rear portion 502 over an entire length thereof.

Figure 35:
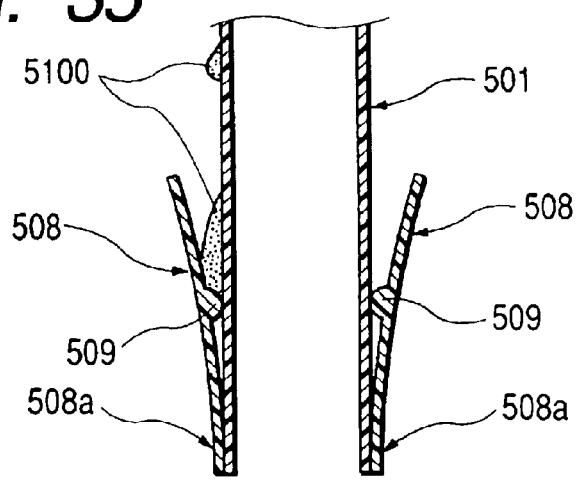
FIG. 35 is a sectional view taken along a line VIII—VIII in FIG. 34 of the cover for preventing contamination of the operating portion of the endoscope according to the modification of the fifth embodiment of the invention.

As shown by FIG. 35 illustrating a section VIII—VIII in FIG. 34, the trough-like member 508 is formed by, for example, welding a strip-like member more rigid than the cover 501 for preventing contamination of the operating portion to the cover 501 for preventing contamination of the operating portion at an outer edge portion 508a thereof and forming a gap in a V-like shape between the trough-like member 508 and the cover 501 for preventing contamination of the operating portion by a projection 509 provided on an inner face side. However, the tough-like member 508 may be constructed by other constitution and the trough-like member 508 may serve also as the edge portion shape maintaining member 504.

Sixth Embodiment

A main feature of a cover for preventing contamination of an operating portion of an endoscope according to this embodiment is such that the cover can cover both of the vicinity of a base end of a light guide cable and an operating portion holding member along with the operating portion in the state of holding the operating portion by the operating portion holding member for holding the operating portion. By this feature, the cover can easily cover the operating portion of the endoscope in the state of holding the operating portion of the endoscope by the holding portion holding member and achieves an excellent effect of eliminating a concern that the inserting portion is contaminated or destructed in operation of covering the operating portion.

Other features and advantages of the cover according to this embodiment are readily understandable from the description directed to this embodiment and/or the description directed to other embodiments.

Figure 37:
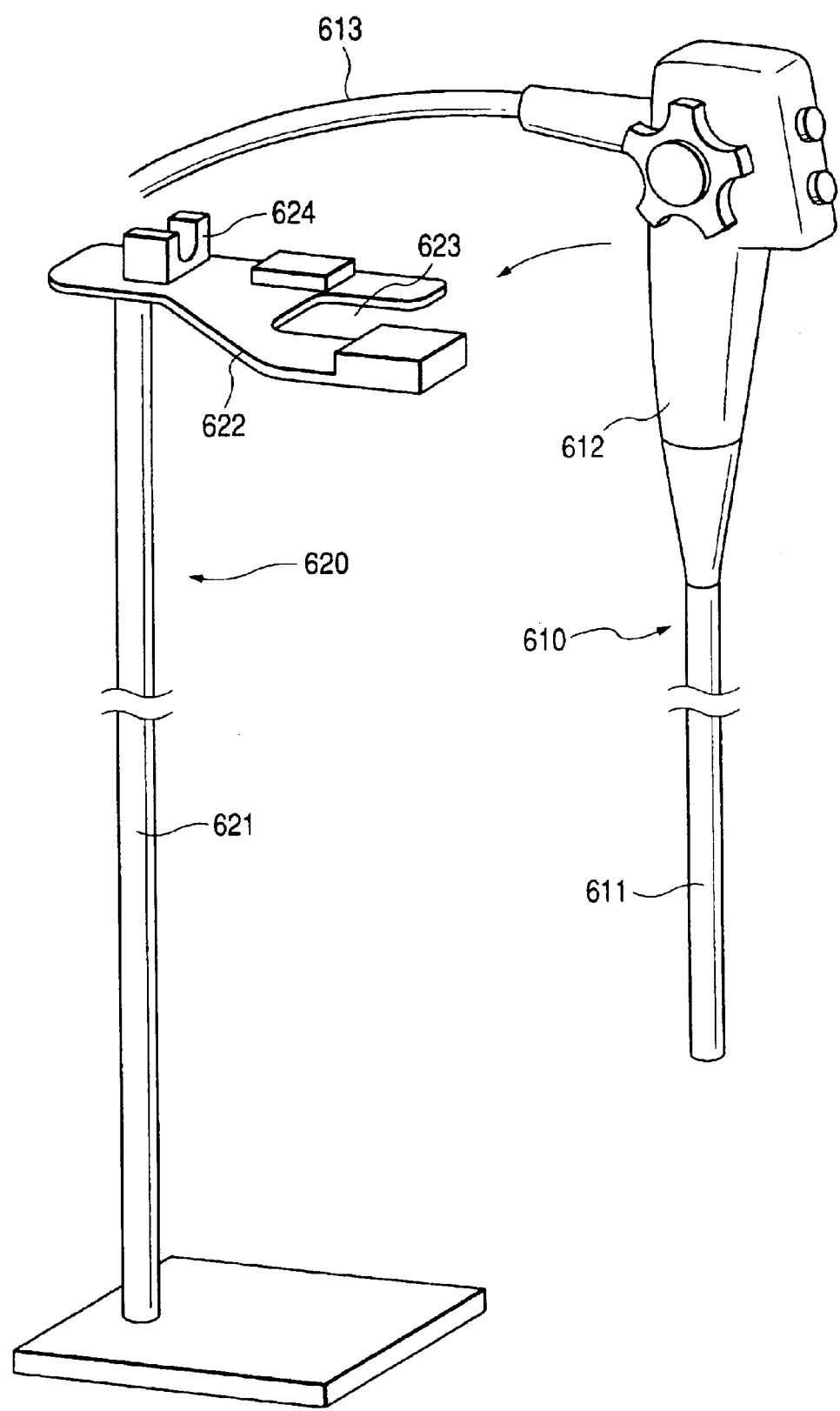
FIG. 37 is a perspective view of an endoscope and an endoscope holding apparatus according to the sixth embodiment of the invention.

FIG. 37 shows an endoscope 610 and an endoscope holding apparatus 620 for holding the endoscope 610 and the endoscope 610 is constructed by a constitution in which a base end of an inserting portion 611 in a shape of a flexible tube is connected to a lower end of an operating portion 612 and a base end of a light guide cable 613 connected to a light source apparatus, not illustrated, is connected to a rear face side portion of the operating portion 612.

According to the embodiment, the endoscope holding apparatus 620 is constructed by a constitution in which an endoscope hanger 622 (endoscope holding member) for holding the operating portion 612 of the endoscope 610 is attached to an upper end portion of a stay 621 vertically arranged and the endoscope hanger 622 is formed with an operating portion engaging groove 623 for engaging the operating portion 612 and a cable guide groove 624 for guiding the light guide cable 613.

Figure 38:
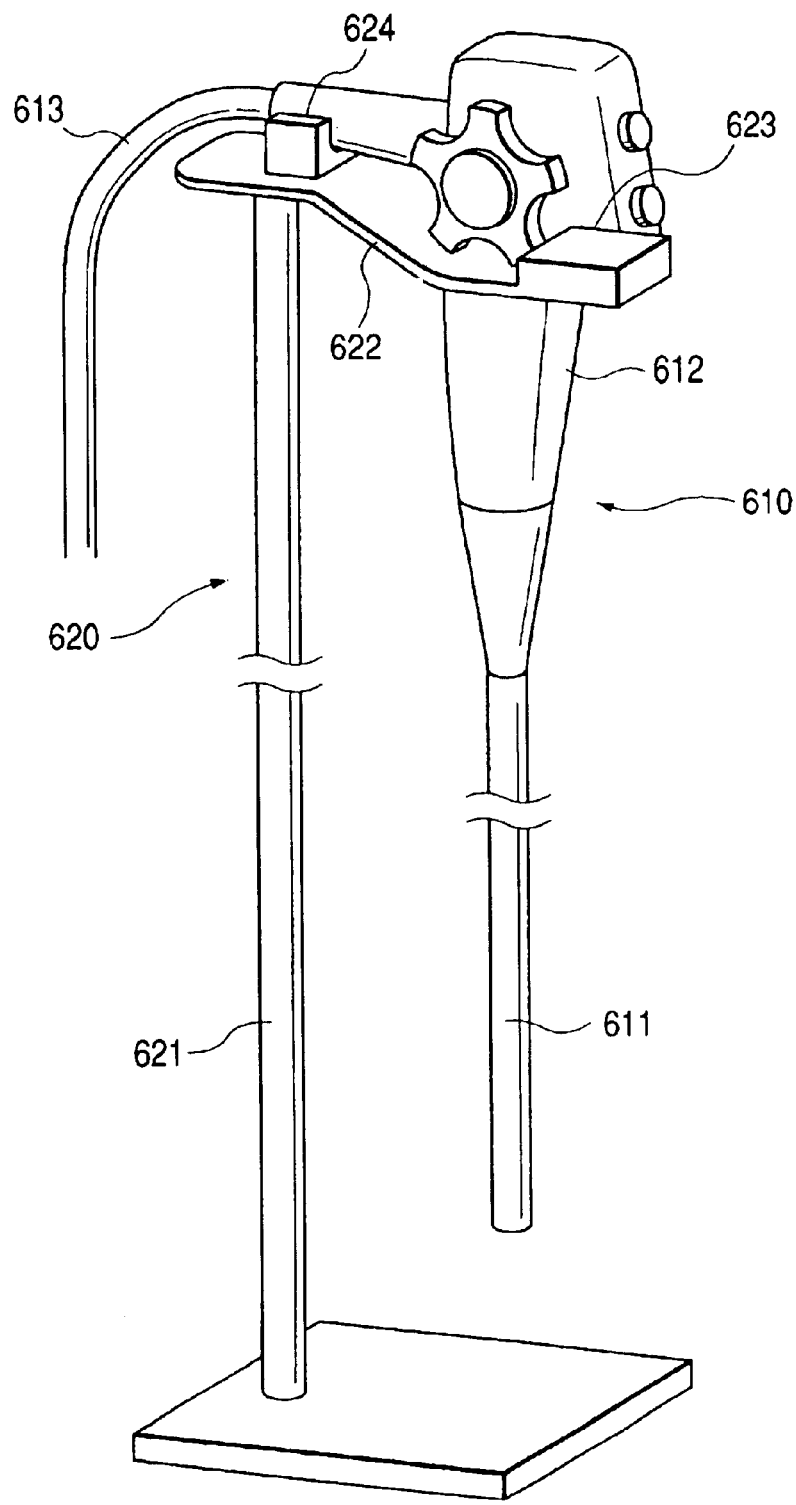
FIG. 38 is a perspective view of a state of holding the endoscope of the sixth embodiment of the invention by the endoscope holding apparatus.

Further, by engaging the operating portion 612 of the endoscope 610 to the operating portion engaging groove 623 of the endoscope holing apparatus 620, as shown by FIG. 38, there is brought about a state in which the operating portion 612 is held by the endoscope hanger 622, the inserting portion 611 hangs down downwardly and the right guide cable 613 is extended to a rear face side of the endoscope hanger 622 along the endoscope hanger 622 by being guided by the cable guide groove 624.

Figure 39:
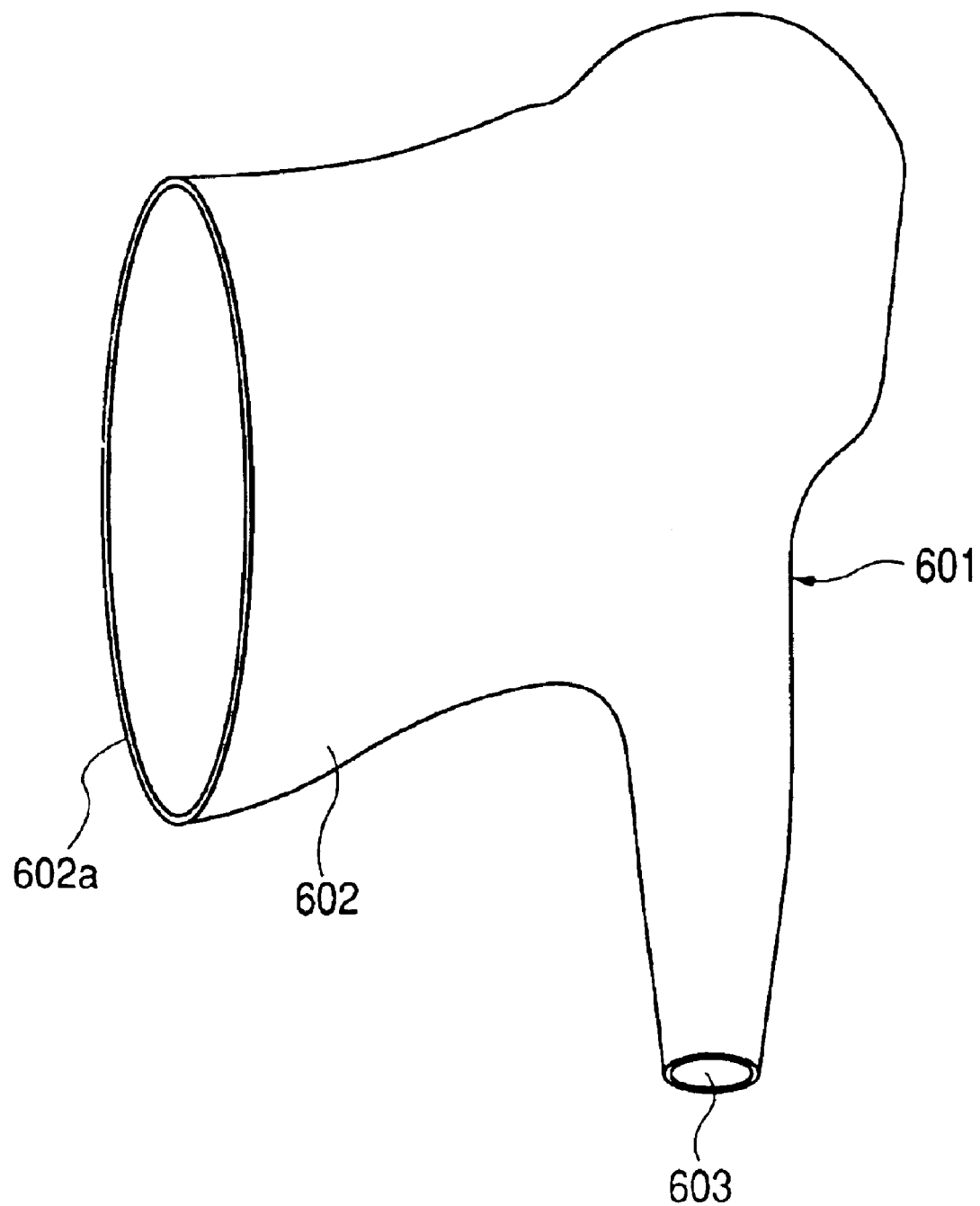
FIG. 39 is a perspective view of the cover for preventing contamination of the operating portion of the endoscope according to the sixth embodiment of the invention.

FIG. 39 shows a cover 601 for preventing contamination of the operating portion according to the embodiment of the invention, the cover 601 for preventing contamination of the operating portion is formed in a bag-like shape for covering a total of the operating portion of the endoscope 610, a rear face side thereof is formed with a sleeve-like portion 602 constituting a state of surrounding the light guide cable 613 and the endoscope hanger 622 and a lower end portion thereof is formed with a small opening 603 for passing the inserting portion 611 of the endoscope 610. Notation 602a designates an end portion opening of the sleeve-like portion 602.

As a material of such a cover 601 for preventing contamination of the operating portion, a sheet of a flexible synthetic resin material of, for example, polyethylene, polypropylene or the like or an elastic rubber material can be used.

Figure 40:
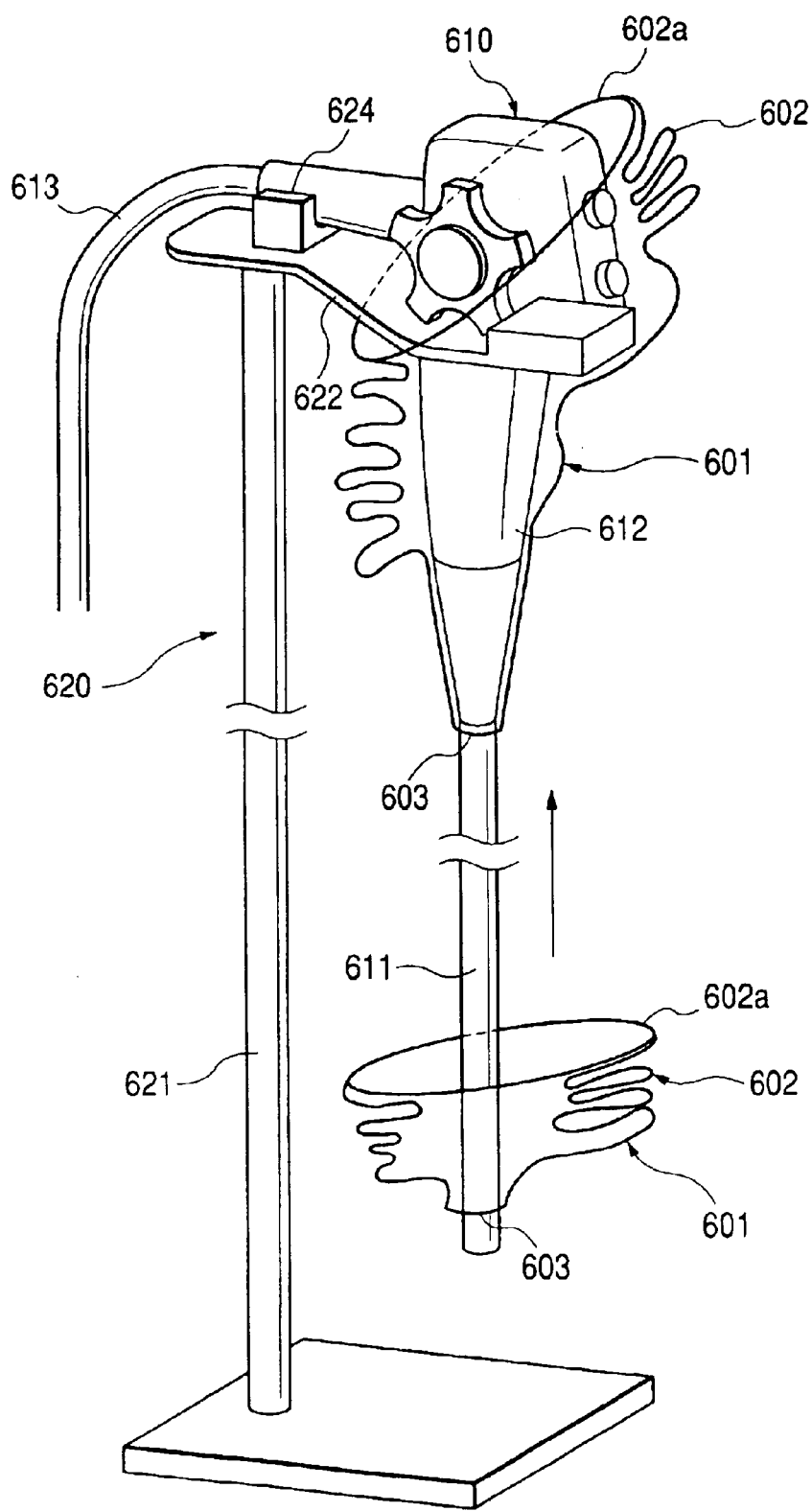
FIG. 40 is a perspective view of a state of operation of covering the cover for preventing contamination of the operating portion of the endoscope according to the sixth embodiment of the invention on the operating portion.

In covering the cover 601 for preventing contamination of the operating portion constituted in this way on the operating portion 612 of the endoscope 610, as shown by FIG. 40 illustrating a state of moving the cover 601 for preventing contamination of the operating portion, in a state in which the operating portion 612 is held by the endoscope hanger 622, the inserting portion 611 of the endoscope 610 is passed from the end portion opening 602a of the sleeve-like portion 602 through the small opening 603 and the cover 601 for preventing contamination of the operating portion is moved to a side of the operating portion 612 along the inserting portion 611. Further, the drawing illustrates a state of viewing through the inner side of the cover 601 for preventing contamination of the operating portion.

Figure 36:
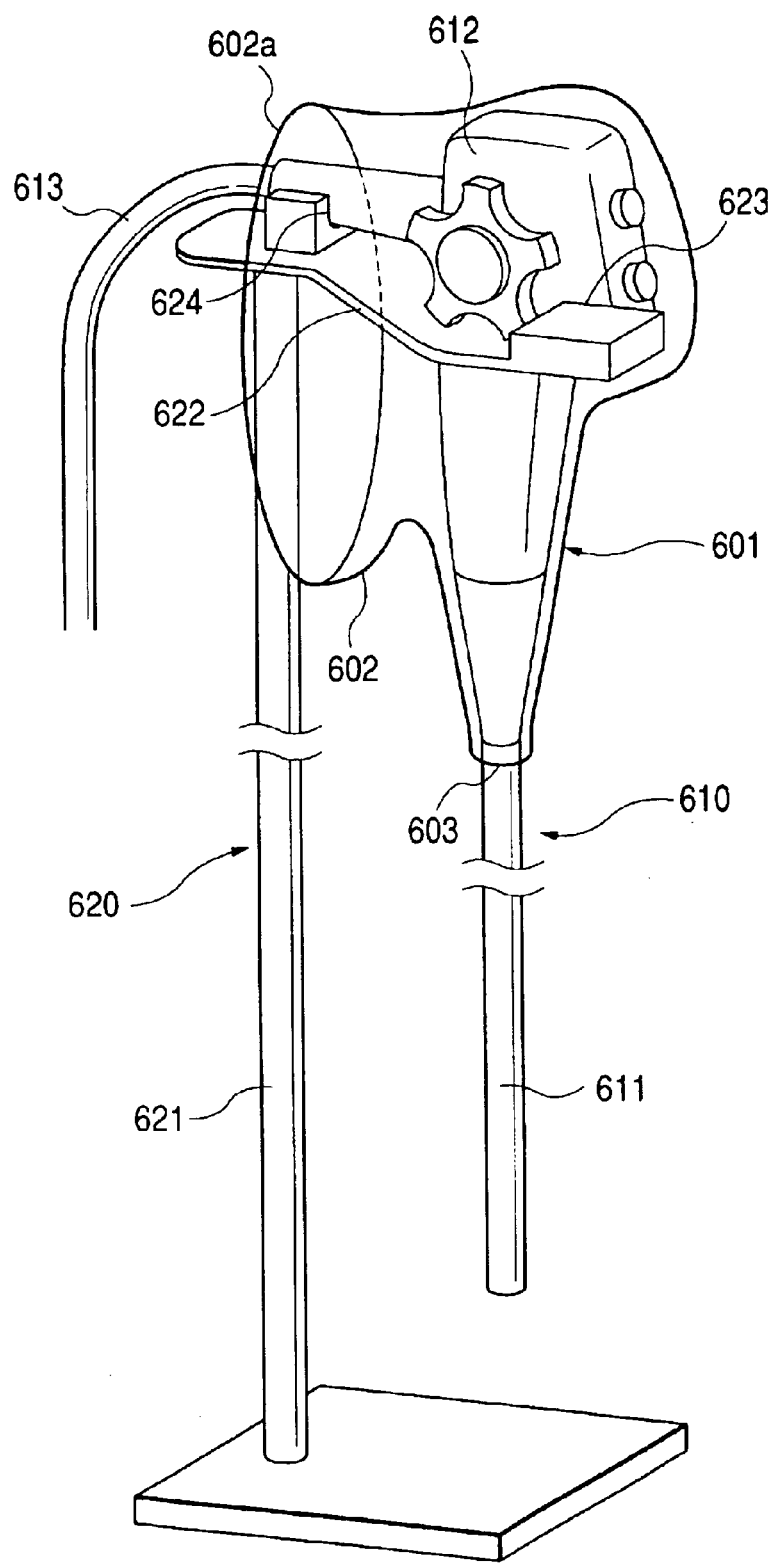
FIG. 36 is a perspective view of a state in which a cover for preventing contamination of an operating portion of an endoscope according to a sixth embodiment of the invention is covered on the operating portion.

When there is brought about a state in which the cover 601 for preventing contamination of the operating portion covers the operating portion 612, as shown by FIG. 36, the cover 601 for preventing contamination of the operating portion is moved until the sleeve-like portion 602 rides over the operating portion 612 and reaches a position surrounding both of the light guide cable 613 and the endoscope hanger 622. The small opening 603 of the cover 601 for preventing contamination of the operating portion is brought into a state of being disposed at a vicinity of a portion of connecting the inserting portion 611 and the operating portion 612.

In this way, by covering both of the vicinity of the end portion of the light guide cable 613 and the endoscope hanger 622 by the sleeve-like portion 602, in a state in which the operating portion 612 is held by the endoscope hanger 622, the operating portion 612 can entirely and completely be covered by the cover 601 for preventing contamination of the operating portion.

Figure 41:
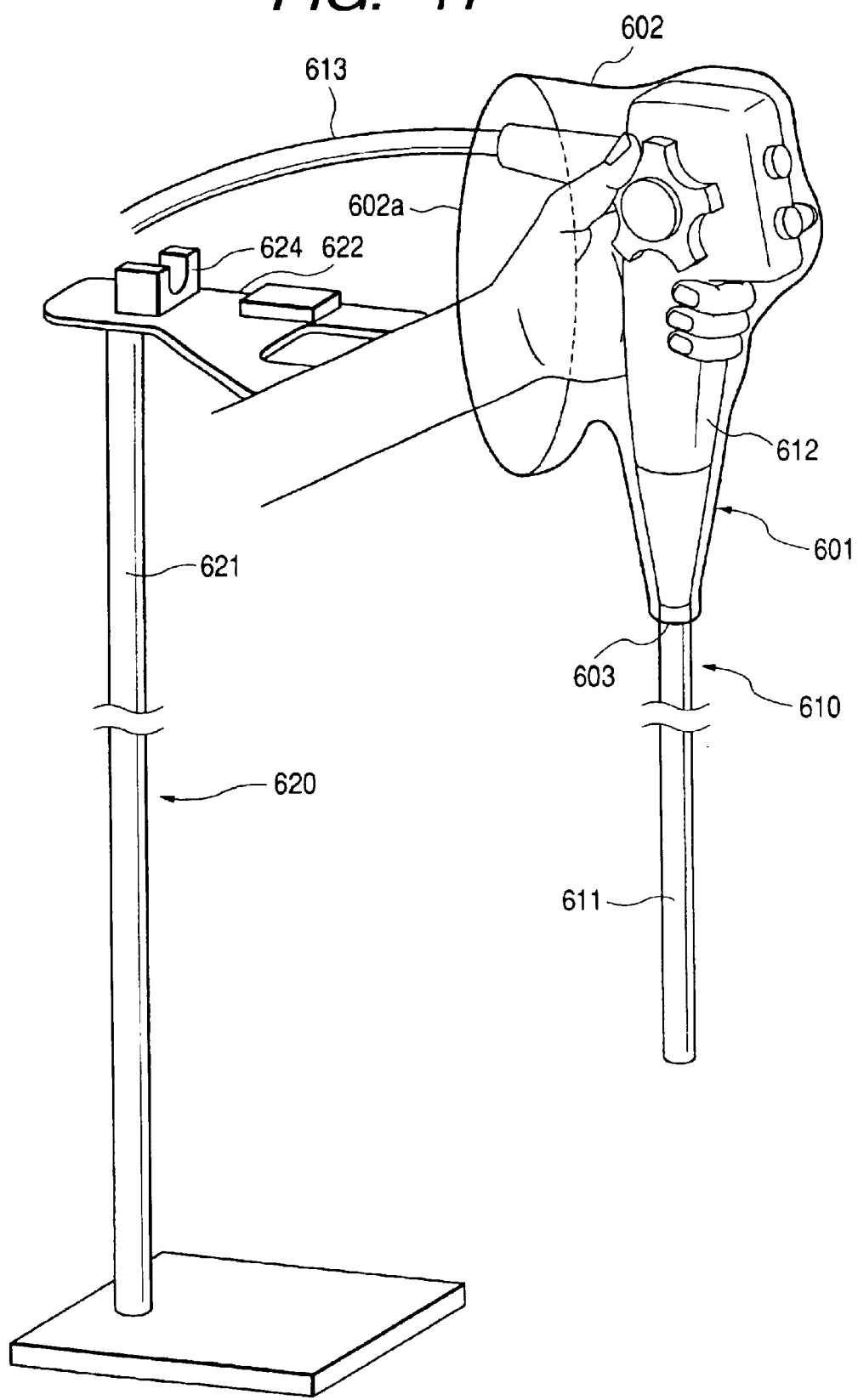
FIG. 41 is a perspective view of a state in which an operator holds the operating portion covered by the cover for preventing contamination of the operating portion of the endoscope according to the sixth embodiment of the invention by the hand.

Further, when the endoscope 610 is used, as shown by FIG. 41, the operator can directly hold the operating portion 612 of the endoscope 610 by inserting the hand from the sleeve-like portion 602 into the cover 601 for preventing contamination of the operating portion.

Figure 42:
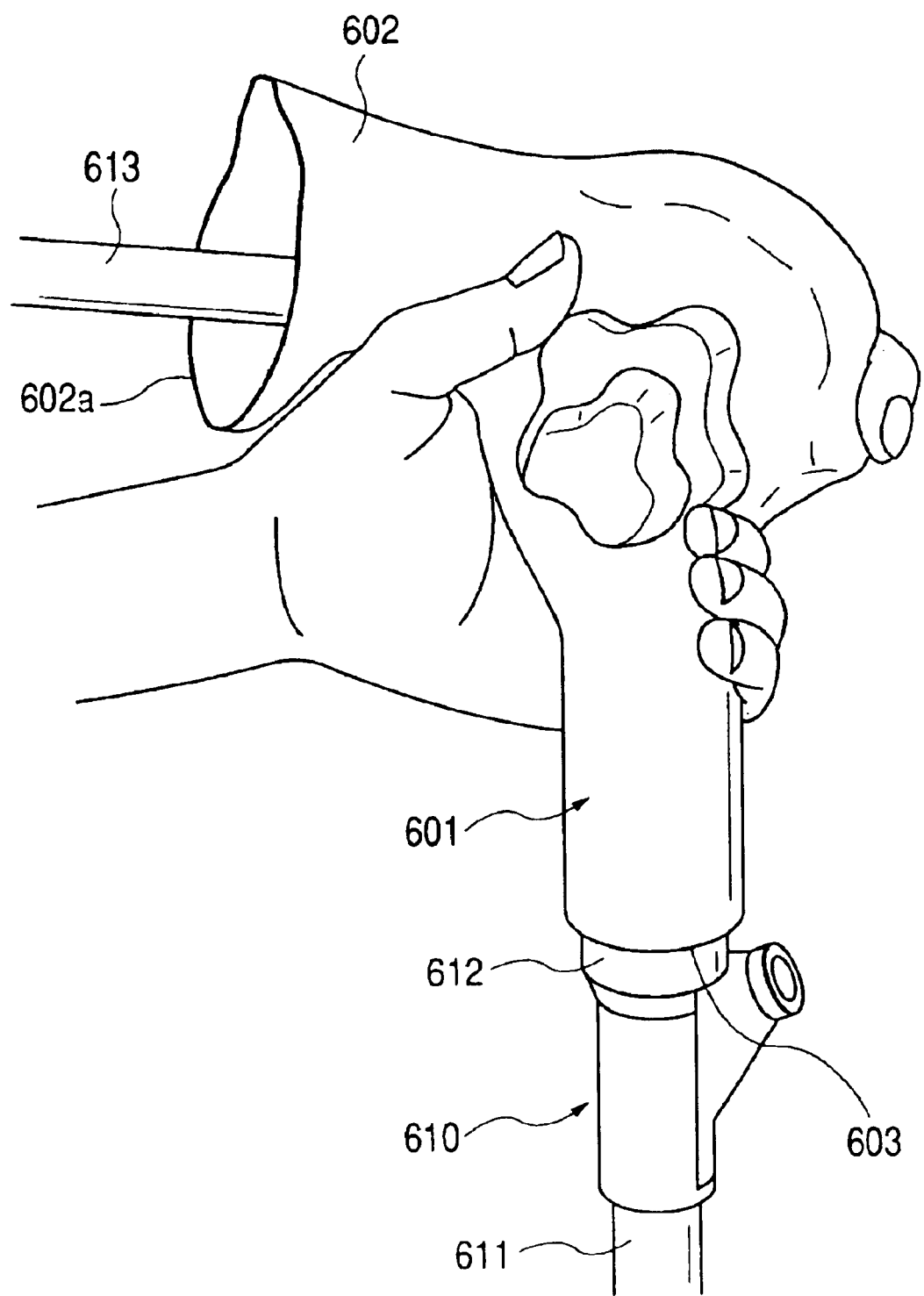
FIG. 42 is a perspective view showing a state in which the operator holds the operating portion covered by the cover for preventing contamination of the operating portion of the endoscope according to a modification of the sixth embodiment of the invention by the hand.

The invention is not limited to the above-described embodiment but, for example, as shown by FIG. 42, the operator may hold the operating portion 612 from an outer side of the cover 601 for preventing contamination of the operating portion for covering the operating portion 612.

Figure 43:
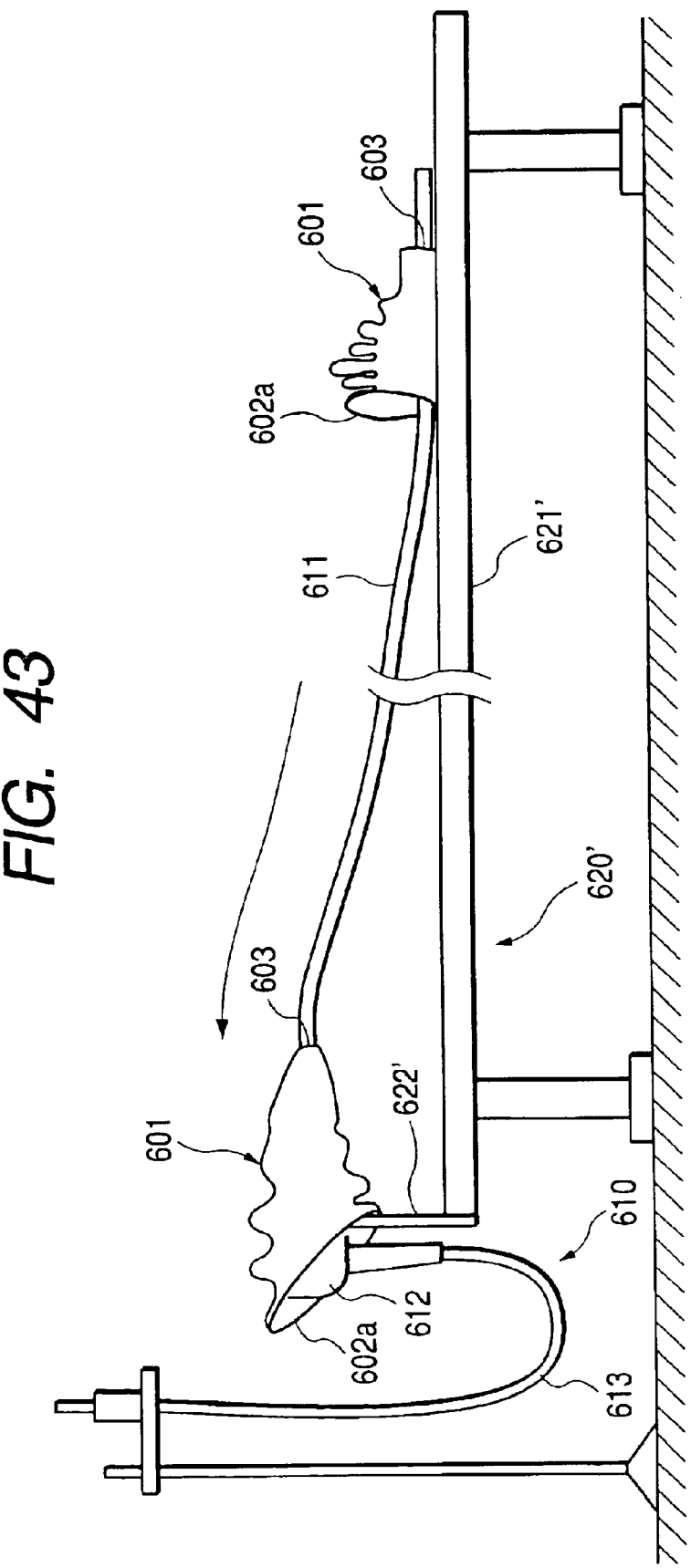
FIG. 43 is a perspective view showing a state of operation of covering a cover for preventing contamination of an operating portion of an endoscope according to another modification of the sixth embodiment of the invention.

Further, as shown by FIG. 43, an endoscope holding apparatus 620' is not limited to a constitution of vertically hanging the endoscope 610 but may be combined with an inserting portion mounting plate 621' and an operating portion holding member 622' for holding the inserting portion 11 and the operating portion 612 respectively in the horizontal direction.

In addition, although the present invention has been discussed with reference to first to sixth embodiments, the present invention should not be restricted thereto or thereby. For example, any one of the above-described main features may be combined with another one of the above-noted main features to thereby constitute a modified cover of the present invention.

What is claimed is:

1. A contamination preventive cover for an endoscope having an operating portion and an insertion portion extending from the operating portion, the cover comprising:

an opening portion, through which the insertion portion of the endoscope can pass, formed at a first end of the cover; and a sleeve portion, defining an opening through which an operator's hand is insertable to directly hold the operation portion enveloped by the cover, positioned at a second end of the cover, wherein the cover is configured to envelope at least the operating portion of the endoscope.

2. The cover according to claim 1, wherein the endoscope has a rotatable bending operating member on the operating portion to permit the operator to remotely perform bending of a tip of the insertion portion, and the cover is further provided with an elastic annular member which tightens the cover toward a rotational axis of the bending operating member at a location between the bending operating member and a surface of the operating portion.

3. The cover according to claim 1, wherein the endoscope has a rotatable bending operating member on the operating portion to permit the operator to remotely perform bending of a tip of the insertion portion, and the cover comprises a closed cylindrical portion that covers the bending operating member and that is deformed to form a bellows at a location between the bending operating member and a surface of the operating portion.

4. The cover according to claim 1, wherein the endoscope has a communication port that is positioned on the operating portion and that communicates with and is connected to a path opened at a tip end of the insertion portion, and the cover comprises an opening through which the communication port protrudes from the cover, and is provided with a fixing member for fixing the cover onto the operating portion so that an opening of the communication port is situated outside the cover.

5. The cover according to claim 1, wherein the first end opening of the cover comprises a closed state maintaining member, and the sleeve portion opening of the cover comprises an edge portion shape maintaining member.

6. The cover according to claim 1, wherein the endoscope is connected, at the operating portion, with a base end of a light guide cable and is configured to be held by an operating portion holding member, and the cover is configured to cover the base end of the light guide cable and the operating portion holding member along with the operating portion.

7. A contamination preventive cover for an endoscope having an operating portion, an insertion portion extending from the operating portion, and a rotatable bending operating member on the operating portion to permit an operator to remotely perform bending of a tip of the insertion portion, the cover comprising:

an elastic annular member which tightens the cover toward a rotational axis of the bending operating member at a location between the bending operating member and a surface of the operating portion, wherein the cover is configured to envelope at least the operating portion of the endoscope.

8. The cover according to claim 7, wherein the cover is configured with a closed cylindrical portion that covers the bending operating member and that is deformed to form a bellows at a location between the bending operating member and a surface of the operating portion.

9. The cover according to claim 7, wherein the endoscope has a communication port that is provided on the operating portion and that communicates with and is connected to a path opened at a tip end of the insertion portion, and the cover comprises an opening through which the communication port protrudes from the cover, and is provided with a fixing member that fixes the cover onto the operating portion so that an opening of the communication port is situated outside the cover.

10. The cover according to claim 7, wherein an opening is provided, at a lower end of the cover, and comprises a closed state maintaining member, and a sleeve portion having an opening is defined at a rear of the cover by an edge portion shape maintaining member.

11. The cover according to claim 7, wherein the endoscope is connected, at the operating portion, with a base end of a light guide cable and is configured to be held by an operating portion holding member, and the cover is configured to cover the base end of the light guide cable and the operating portion holding member along with the operating portion.

12. A contamination preventive cover for an endoscope having an operating portion, an insertion portion extending from the operating portion, and a rotatable bending operating member on the operating portion that permits an operator to remotely perform bending of a tip of the insertion portion, the cover comprising:

a closed cylindrical portion that covers the bending operating member and that is deformed to form a bellows at the location between the bending operating member and the surface of the operating portion, wherein the cover is configured to envelope at least the operating portion of the endoscope.

13. The cover according to claim 12, wherein the endoscope has a communication port that is positioned on the operating portion and that communicates with and is connected to a path opened at a tip end of the insertion portion, and the cover comprises an opening through which the communication port protrudes from the cover, and is provided with a fixing member that fixes the cover onto the operating portion so that an opening of the communication port is situated outside the cover.

14. The cover according to claim 12, wherein an opening is provided, at a lower end of the cover, and comprises a closed state maintaining member, and a sleeve portion having an opening is defined at a rear of the cover by an edge portion shape maintaining member.

15. The cover according to claim 12, wherein the endoscope is connected, at the operating portion, with a base end of a light guide cable and is configured to be held by an operating portion holding member, and the cover is configured to cover the base end of the light guide cable and the operating portion holding member along with the operating portion.

16. A contamination preventive cover for an endoscope having an operating portion, an insertion portion extending from the operating portion and a communication port that is provided on the operating portion and that communicates with and is connected to a path opened at a tip end of the insertion portion, the cover comprising:

an opening portion through which the communication port protrudes from the cover; and a fixing member that fixes the cover onto the operating portion so that an opening of the communication port is situated outside the cover, wherein the cover is configured to envelope at least the operating portion of the endoscope.

17. The cover according to claim 16, wherein an opening is provided, at a lower end of the cover, and comprises a closed state maintaining member, and a sleeve portion having an opening is defined at a rear of the cover by an edge portion shape maintaining member.

18. The cover according to claim 16, wherein the endoscope is connected, at the operating portion, with a base end of a light guide cable and is configured to be held by an operating portion holding member, and the cover is configured to cover the base end of the light guide cable and the operating portion holding member along with the operating portion.

19. A contamination preventive cover for an endoscope having an operating portion and an insertion portion extending from the operating portion, the cover comprising:

a continuous opening portion extending from a side of the cover to a lower end of the cover, an edge portion shape maintaining member being positioned along an opening edge portion of the side;

a closed state maintaining member positioned in a lower half portion of the side of the cover, and wherein the continuous opening is configured by the edge portion shape maintaining member and the closed state maintaining member to define an opening at the lower end of the cover; and another opening at an upper half of the side of the cover, wherein the cover is configured to envelope at least the operating portion of the endoscope.

20. The cover according to claim 19, wherein the endoscope is connected, at the operating portion, with a base end of a light guide cable and is configured to be held by an operating portion holding member, and the cover is configured to cover the base end of the light guide cable and the operating portion holding member along with the operating portion.

21. A contamination preventive cover for an endoscope having an operating portion and an insertion portion extending from the operating portion, wherein the endoscope is connected, at the operating portion, with a base end of a light guide cable and is configured to be held by an operating portion holding member, and the cover is configured to cover the base end of the light guide cable and the operating portion holding member along with the operating portion.

22. The cover according to claim 1, wherein the opening defined in the sleeve portion has a cylindrical shape.

* * * * *